US010328267B2

(12) United States Patent
Hatlestad et al.

(10) Patent No.: US 10,328,267 B2
(45) Date of Patent: Jun. 25, 2019

(54) METHODS FOR CONSTRUCTING POSTURE CALIBRATION MATRICES

(75) Inventors: John D. Hatlestad, Maplewood, MN (US); Tsz Ping Chang, Baltimore, MD (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1756 days.

(21) Appl. No.: 13/024,823

(22) Filed: Feb. 10, 2011

(65) Prior Publication Data
US 2011/0201969 A1     Aug. 18, 2011

Related U.S. Application Data

(60) Provisional application No. 61/304,649, filed on Feb. 15, 2010.

(51) Int. Cl.
*A61N 1/365*     (2006.01)
*A61B 5/11*      (2006.01)
(Continued)

(52) U.S. Cl.
CPC ........ *A61N 1/36542* (2013.01); *A61B 5/1116* (2013.01); *A61B 5/1117* (2013.01);
(Continued)

(58) Field of Classification Search
CPC .............................. A61B 5/4528; A61B 5/103
(Continued)

(56) References Cited

U.S. PATENT DOCUMENTS 5,593,431 A    1/1997 Sheldon
6,044,297 A    3/2000 Sheldon et al.
(Continued)

FOREIGN PATENT DOCUMENTS

AU    2011215822 B2    9/2013
EP       2536334 B1    12/2013
(Continued)

OTHER PUBLICATIONS

International Application Serial No. PCT/US2011/024339, International Preliminary Report on Patentability dated Aug. 30, 2012, 7 pgs.
(Continued)

*Primary Examiner* — Daniel L Cerioni
(74) *Attorney, Agent, or Firm* — Schwegman, Lundberg & Woessner

(57) ABSTRACT

A device can include a multi-dimensional posture sensor that provides an electrical sensor output representative of alignment of first, second, and third non-parallel axes of the device with the gravitational field of the earth, and a processor that includes a calibration circuit and a posture circuit. The calibration circuit measures a first sensor output for the first device axis and a second sensor output for one of a second device axis while the subject is in a first specified posture, measures sensor outputs for the first, second, and third device axes while the subject is in a second specified posture, calculates one or more coordinate transformations, generates transformed sensor outputs using the coordinate transformations, and calibrates the posture sensor by calculating a calibration transformation using the first and second sensor outputs and the transformed sensor outputs. The posture circuit determines a subsequent posture of the subject using the posture sensor.

20 Claims, 10 Drawing Sheets

BODY COORDINATES (X, Y, Z)      DEVICE COORDINATES (U, V, W)

(51) Int. Cl.
*G01P 15/18* (2013.01)
*A61N 1/39* (2006.01)
*A61B 5/00* (2006.01)

(52) U.S. Cl.
CPC ............ *A61B 5/1118* (2013.01); *G01P 15/18* (2013.01); *A61B 5/686* (2013.01); *A61B 2560/0223* (2013.01); *A61B 2562/0219* (2013.01); *A61N 1/3925* (2013.01)

(58) Field of Classification Search
USPC ........................................................ 600/587
See application file for complete search history.

(56) References Cited

U.S. PATENT DOCUMENTS

| | | | |
|---|---|---|---|
| 6,076,015 | A | 6/2000 | Hartley et al. |
| 7,149,579 | B1 | 12/2006 | Koh et al. |
| 7,149,584 | B1 | 12/2006 | Koh et al. |
| 8,708,934 | B2 * | 4/2014 | Skelton et al. ............... 600/595 |
| 2007/0032748 | A1 * | 2/2007 | McNeil et al. ............... 600/595 |
| 2007/0115277 | A1 | 5/2007 | Wang et al. |
| 2007/0118056 | A1 | 5/2007 | Wang et al. |
| 2008/0091373 | A1 * | 4/2008 | McGibbon et al. ............ 702/95 |
| 2008/0288200 | A1 | 11/2008 | Noble |
| 2009/0312973 | A1 * | 12/2009 | Hatlestad et al. ............. 702/85 |
| 2011/0313327 | A1 * | 12/2011 | Van Acht et al. ............ 600/595 |

FOREIGN PATENT DOCUMENTS

| | | |
|---|---|---|
| JP | 2009515662 A | 4/2009 |
| JP | 2009276094 A | 11/2009 |
| WO | WO-00/18317 A2 | 4/2000 |
| WO | WO-2000018317 A2 | 4/2000 |
| WO | WO-2007/061746 A2 | 5/2007 |
| WO | WO-2011/100422 A1 | 8/2011 |

OTHER PUBLICATIONS

"International Application Serial No. PCT/US2011/024339, International Search Report dated May 24, 2011", 4 pgs.

"International Application Serial No. PCT/US2011/024339, Written Opinion dated May 24, 2011", 7 pgs.

Brown, G., "An Accelerometer Based Fall Detector : Development, Experimentation, and Analysis", [online]. 1985, EECS/SUPERB [retrieved Feb. 13, 2008]. Retrieved from the Internet: <URL: http://bsn.citris.berkeley.edu/media/GarrettFinalPaper.pdf>, (Jul. 2005), 9 pgs.

"Australian Application Serial No. 2011215822, First Examiner Report dated Feb. 5, 2013", 3 pgs.

"Japanese Application Serial No. 2012-552995, Office Action dated Sep. 2, 2014", With English Translation, 5 pgs.

"Japanese Application Serial No. 2012-552995, Office Action dated Dec. 24, 2013", With English Translation, 8 pgs.

* cited by examiner

METHODS FOR CONSTRUCTING POSTURE CALIBRATION MATRICES

CROSS-REFERENCE TO RELATED APPLICATIONS

This application claims the benefit of U.S. Provisional Application No. 61/304,649, filed on Feb. 15, 2010, under 35 U.S.C. § 119(e), which is incorporated herein by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices also include wearable medical devices (WMDs) such as wearable cardioverter defibrillators (WCDs). WCDs are monitors that include surface electrodes. The surface electrodes are arranged to provide one or both of monitoring surface electrocardiograms (ECGs) and delivering cardioverter and defibrillator shock therapy.

Some IMDs include one or more sensors to monitor different physiologic aspects of the patient. Sensing of patient posture can provide information related to a patient's condition or disease. For example, a patient with congestive heart failure (CHF) may tend to sleep in an upward position as their condition worsens. Patient posture information may also be useful in other aspects of patient monitoring. For example, measurements taken by a medical device may vary with patient posture. Knowledge of the posture of the patient during the measurements may be useful to a caregiver in interpreting the device measurements.

OVERVIEW

This document relates generally to systems, devices, and methods for determining posture in a patient or subject. In particular it relates to, systems, devices, and methods that calibrate a posture sensing device for varying orientation that results from mounting or implanting the posture sensing device.

Example 1 can include a device that comprises a multi-dimensional posture sensor configured to provide an electrical sensor output representative of alignment of respective first, second, and third non-parallel axes of the device with the gravitational field of the earth, a processor that includes a calibration circuit and a posture circuit. The calibration circuit can be configured to measure a first sensor output for the first device axis and a second sensor output for one of the second or third device axes while the subject is in a first specified posture, measure sensor outputs for the first, second, and third device axes while the subject is in a second specified posture, calculate one or more coordinate transformations using a sensor output from the first specified posture, transform the sensor outputs for the second posture using the coordinate transformations, and calibrate the posture sensor by calculating a calibration transformation using the first and second sensor outputs and the transformed sensor outputs. The posture circuit can be configured to determine a subsequent posture of the subject using the posture sensor.

In Example 2, the subject matter of Example 1 can optionally include the calibration circuit being configured to calculate a first coordinate transformation associated with a first orientation angle using the first sensor output, calculate a second coordinate transformation associated with a second orientation angle using the first sensor output and the second sensor output, measure third, fourth, and fifth sensor outputs for respective first, second, and third device axes while the subject is in the second specified posture, and transform the third, fourth, and fifth sensor outputs using the first and second coordinate transformations.

In Example 3, the subject matter of any one of Examples 1-2 can optionally include the calibration circuit being configured to calculate elements of a first rotation matrix using the first sensor output, calculate elements of a second rotation matrix using the first sensor output and the second sensor output, and multiply the third, fourth, and fifth sensor outputs by the first and second rotation matrices to transform the sensor outputs.

In Example 4, the subject matter of any one of Examples 1-3 can optionally include the calibration circuit being configured to calculate a calibration transformation by calculating elements of a calibration matrix.

In Example 5, the subject matter of any one of Examples 1-4 can optionally include the calibration circuit being configured to calculate a first set of matrix components related to a first orientation angle using the first sensor output, calculate a second set of matrix components related to a second orientation angle using the first sensor output and one of the second sensor output or the third sensor output, calculate a third set of matrix components related to a third orientation angle using the transformed sensor outputs, and calculate the elements of the calibration matrix using the first, second, and third sets of matrix components.

In Example 6, the subject matter of any one of Examples 1-5 can optionally include the calibration circuit being configured to calculate the first set of matrix components related to a first orientation angle associated with a pitch angle, calculate a second set of matrix components related to a second orientation angle associated with a roll angle, and calculate a third set of matrix components related to a third orientation angle associated with a yaw angle.

In Example 7, the subject matter of any one of Examples 1-6 can optionally include the calibration circuit being configured to calculate the first set of matrix components related to a first orientation angle associated with a pitch angle, calculate a second set of matrix components related to a second orientation angle associated with a roll angle, and calculate a third set of matrix components related to a third orientation angle associated with a roll angle.

In Example 8, the subject matter of any one of claims 1-7 can optionally include the posture circuit being configured to receive a sensor output for each of the three non-parallel axes of the posture sensor, transform the sensor outputs using the calibration transformation, and compare the transformed sensor outputs to specified thresholds to determine posture of the subject.

In Example 9, the subject matter of any one of Examples 1-8 can optionally include the second posture being a posture non-orthogonal to the first posture.

In Example 10, the subject matter of any one of Examples 1-9 can optionally include the first posture being an upright posture, and the second posture being optionally more supine than the first posture and less than fully supine.

In Example 11, the subject matter of any one of Examples 1-10 can optionally include the first posture being a supine posture, and the second posture being optionally more upright than the first posture and less than fully upright.

Example 12 can include, or can be combined with the subject matter of any one of Examples 1-10 to optionally include, subject matter that can comprise measuring a first sensor output for the first device axis and a second sensor output for one of the second or third device axes while the subject is in a first specified posture, measuring sensor outputs for the first, second and third device axes while the subject is in a second specified posture, calculating one or more coordinate transformations using a sensor output from the first specified posture, transforming the sensor outputs using the coordinate transformations, and calibrating the posture sensor by calculating a calibration transformation using the first and second sensor outputs and the transformed sensor outputs. The calibration can be used to determine subsequent subject posture from subsequent sensor output.

In Example 13, the subject matter of any one of Examples 1-12 can optionally include calculating one or more coordinate transformations using a sensor output from the first specified posture, which can optionally include calculating, using the first sensor output, a first coordinate transformation associated with a first orientation angle, calculating, using the first sensor output and the second sensor output, a second coordinate transformation associated with a second orientation angle, wherein measuring sensor outputs for the first, second and third device axes includes measuring third, fourth, and fifth sensor outputs for respective first, second and third device axes while the subject is in the second specified posture, and wherein transforming outputs includes transforming the third, fourth, and fifth sensor outputs using the first and second coordinate transformations.

In Example 14, the subject matter of any one of Examples 1-13 can optionally include calculating the first coordinate transformation including calculating elements of a first rotation matrix using the first sensor output, the calculating the second coordinate transformation optionally includes calculating elements of a second rotation matrix using the first sensor output and the second sensor output, and the transforming the third, fourth, and fifth sensor outputs optionally includes multiplying the third, fourth, and fifth sensor outputs by the first and second rotation matrices to transform the sensor outputs.

In Example 15, the subject matter of any one of Examples 1-14 can optionally include calculating a calibration transformation including calculating elements of a calibration matrix, and the using the calibration to determine subsequent subject posture optionally includes using the calibration matrix to determine subsequent subject posture from subsequent sensor output.

In Example 16, the subject matter of any one of Examples 1-15 can optionally include calculating elements of a matrix to calibrate the posture sensor using sensor outputs, including calculating a first set of matrix components related to a first orientation angle using the first sensor output, calculating a second set of matrix components related to a second orientation angle using the first sensor output and the second sensor output, calculating a third set of matrix components related to a third orientation angle using the transformed sensor outputs, and calculating the elements of the calibration matrix using the first, second, and third sets of matrix components.

In Example 17, the subject matter of any one of Examples 1-16 can optionally include calculating a first set of matrix components related to a first orientation angle, including calculating a first set of matrix components associated with a pitch angle, the calculating a second set of matrix components related to a second orientation angle optionally includes calculating a second set of matrix components associated with a roll angle, and the calculating a third set of matrix components related to a third orientation angle optionally includes calculating a second set of matrix components associated with a yaw angle.

In Example 18, the subject matter of any one of Examples 1-17 can optionally include calculating a first set of matrix components related to a first orientation angle, optionally including calculating a first set of matrix components associated with a pitch angle, the calculating a second set of matrix components related to a second orientation angle includes calculating a second set of matrix components associated with a yaw angle, and the calculating a third set of matrix components related to a third orientation angle includes calculating a second set of matrix components associated with a roll angle.

In Example 19, the subject matter of any one of Examples 1-18 can optionally include measuring while the subject is in a second specified posture, optionally including measuring while the subject is in a second specified posture that is non-orthogonal to the first specified posture.

In Example 20, the subject matter of any one of Examples 1-19 can optionally include using the calibration to determine subsequent subject posture, optionally including receiving a sensor output for each of three orthogonal axes of the multi-dimensional sensor, transforming the sensor outputs to body coordinate values using the calibration transformation, and comparing the sensor outputs to specified thresholds to determine the posture.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

A medical device (e.g., an IMD or WMD) can include one or more of the features, structures, methods, or combinations thereof described herein. For example, a cardiac monitor or a cardiac stimulator can be implemented to include one or more of the advantageous features or processes described below. It is intended that such a monitor, stimulator, or other implantable or partially implantable device need not include all of the features described herein, but can be implemented to include selected features that provide for unique structures or functionality. Such a device can be implemented to provide a variety of therapeutic or diagnostic functions.

Posture sensing with a medical device can improve patient monitoring. Examples of a posture sensor include a multi-axis accelerometer and a tilt switch. With a posture sensor, a medical device can detect whether a patient is in an upright position, a supine position, a prone position, on his or her left or right side, or if the patient is in a tilted position. For patients with heart failure, posture sensing allows monitoring of orthopnea; a condition where the patient can breathe easily only when in an upright posture (e.g., standing or sitting with the torso upright). Posture sensing also allows monitoring of Paroxysmal Nocturnal Dyspnea (PND); a condition including labored or difficult breathing that awakens patients from sleep.

Posture sensing can also improve the use of other sensors used to monitor a patient's cardiac activity. For example, heart sounds are associated with mechanical activity of a patient's heart. The amplitude of heart sounds can vary with patient posture as well as cardiac disease. Knowledge of patient posture can improve monitoring of patient heart sounds. In another example, pulmonary arterial (PA) pressure is useful to monitor a patient's cardiac disease, but varies with patient posture. Patient posture information can improve monitoring of PA pressure by determining whether PA pressure variation is due to posture or to disease.

Orientation of a medical device can vary from patient to patient. This complicates the automatic determination of patient posture by the medical device. For instance, for an implantable device the orientation of the IMD in the body is unknown. Because physiology varies among patients, a pacemaker can have a different orientation from patient to patient due to differences in angles of the chest of the patients. Also, an IMD can undergo some rotation or other migration over the life of the device. Calibration of the posture sensor compensates for the unknown angle of an IMD in a body or for a changing angle of a WMD.

Figure 1:
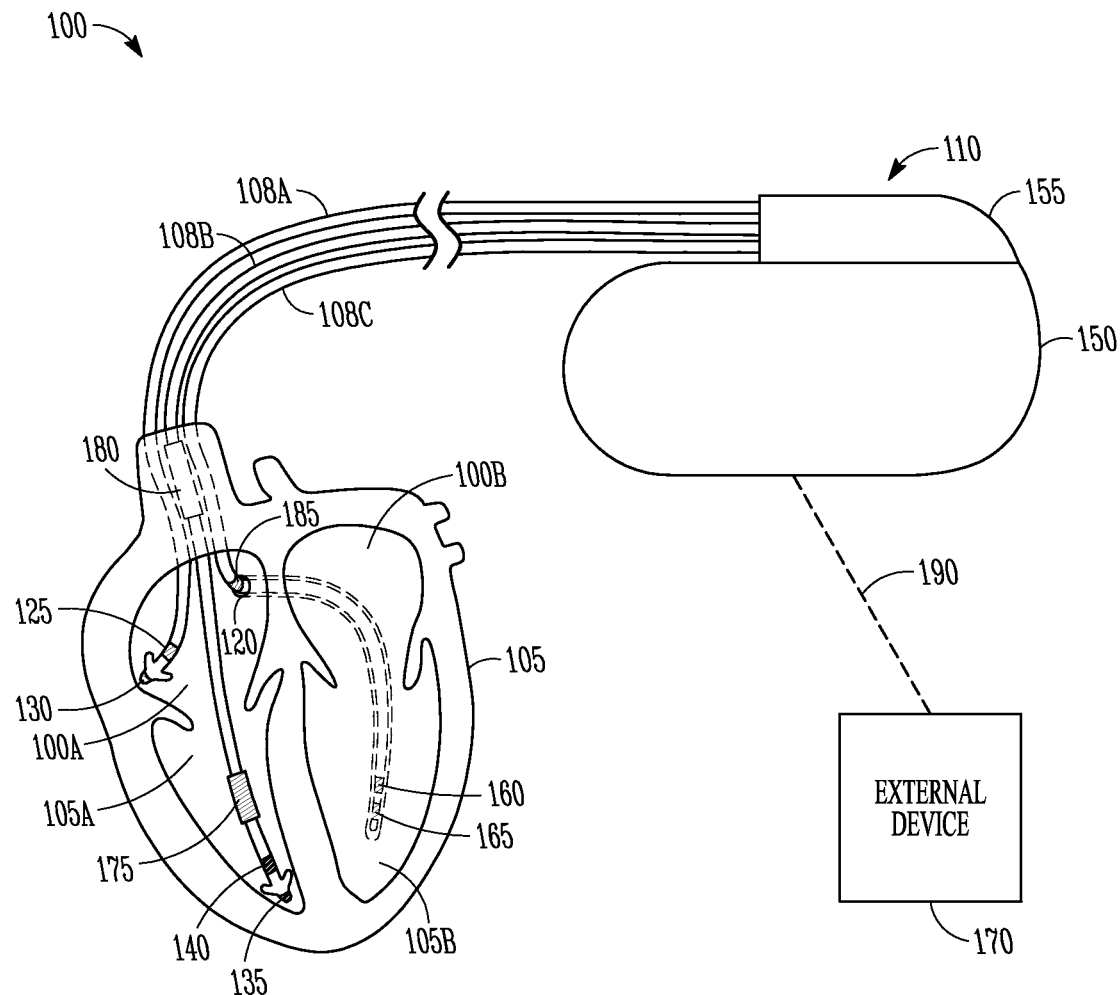
FIG. 1 is an illustration of an example of portions of a system that includes an IMD.

FIG. 1 is an illustration of portions of a system 100 that uses an IMD 110 or other ambulatory medical device. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 is coupled by one or more leads 108A-C to heart 110. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes can be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 can include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein. The third cardiac lead 108C can include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150.

Note that although a specific arrangement of leads and electrodes are shown the illustration, the present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

An IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Figure 2:
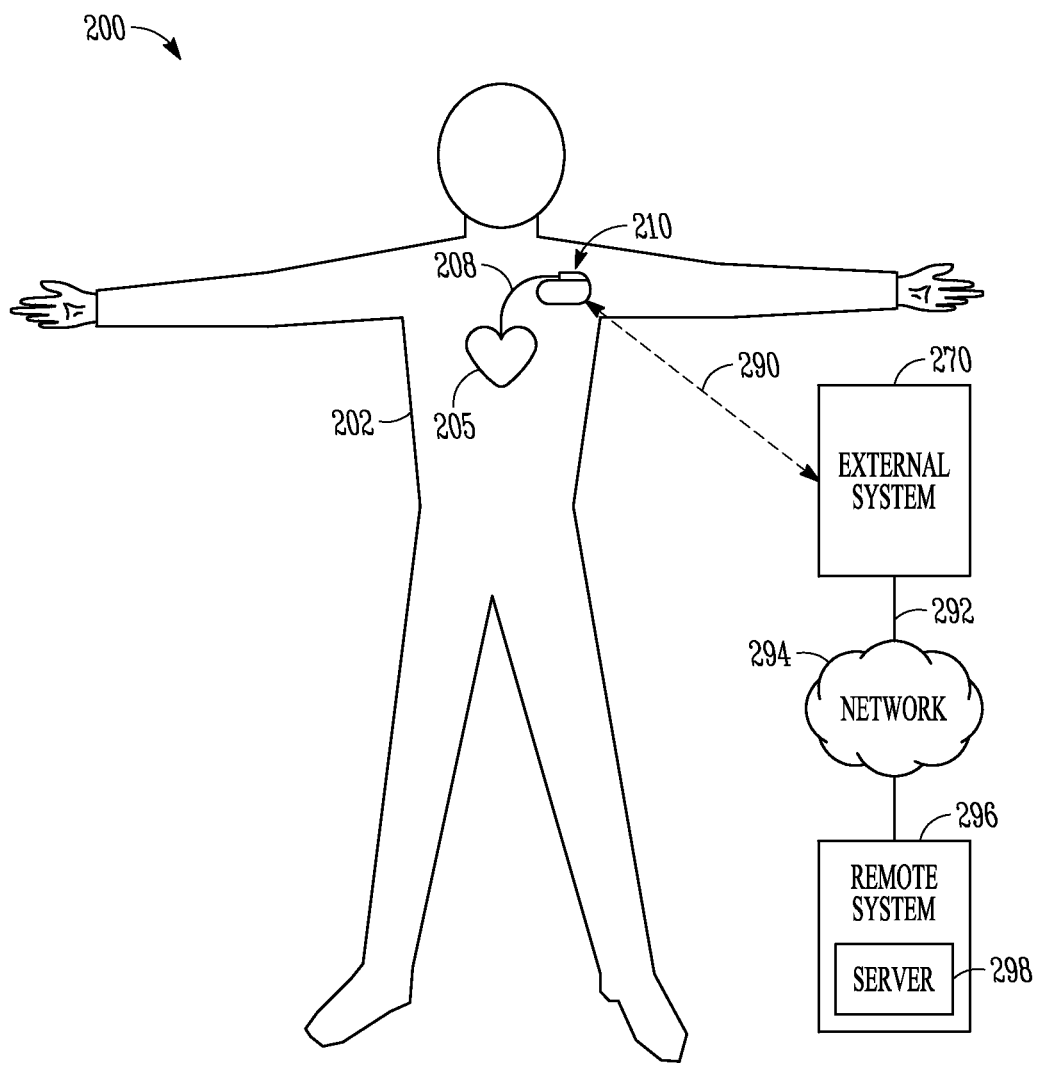
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that can be wired or wireless. In some examples, the remote system 296 provides patient management functions and can include one or more servers 298 to perform the functions.

Figure 3A:
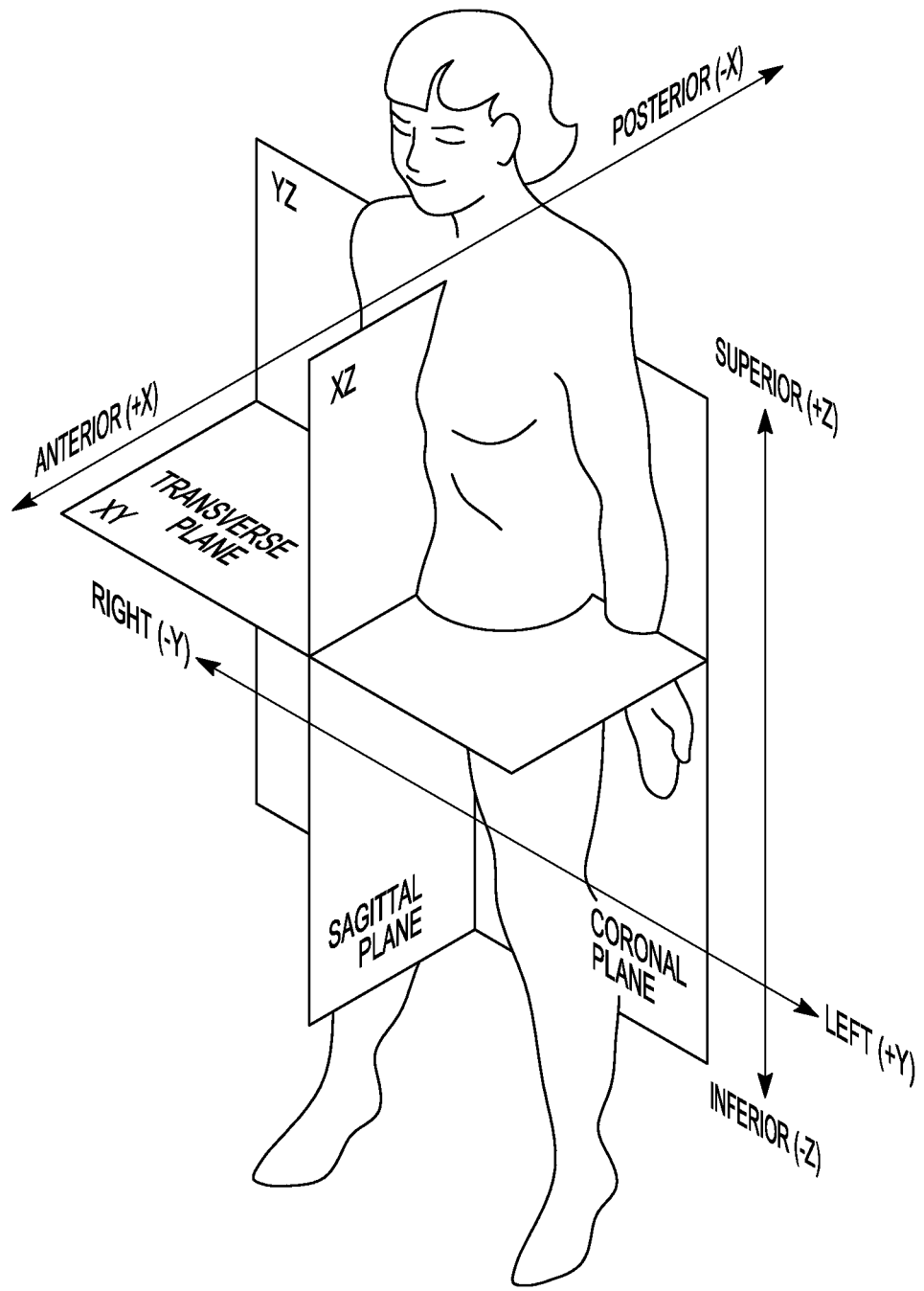
FIGS. 3A and 3B illustrate a coordinate system for a patient's body.
Figure 3B:
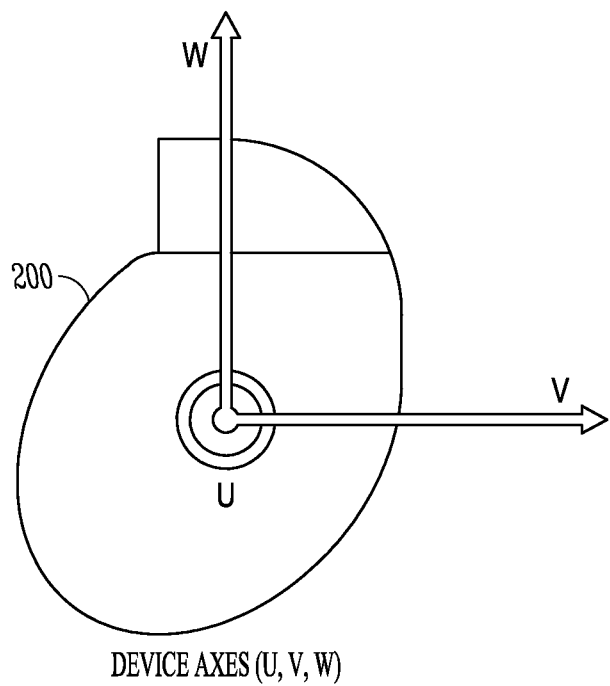

FIG. 3 shows a coordinate system for a patient's body. The body coordinate system uses the x, y, and z axes to describe the posterior to anterior direction, left to right direction, and inferior to superior direction respectively. FIG. 3 also shows a device coordinate system using u, v, and w axes as shown. A desirable orientation of the device 300 can be in the coronal plane such that the device axes match the body axes (e.g., u↔x, v↔y, w↔z). However, a device orientation is not typically in an ideal orientation.

Figure 4:
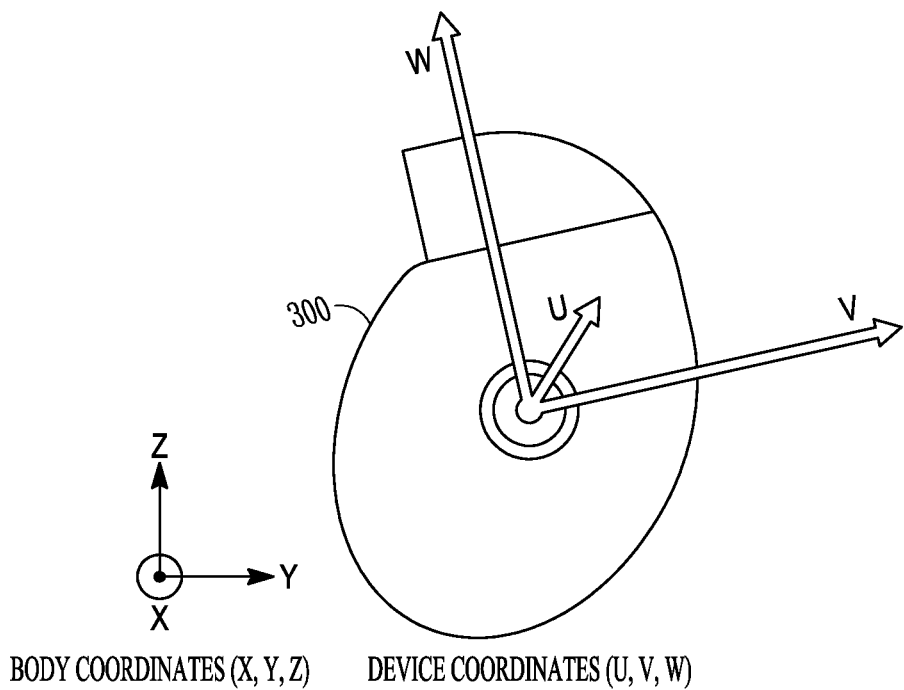
FIG. 4 illustrates device coordinates that are skewed from the body coordinates.

FIG. 4 shows the more typical case in which the device coordinates are skewed from the body coordinates. As discussed previously, this can be due to patient anatomy or due to movement of the implanted or worn medical device 400. A calibration procedure is used to determine the device orientation or to translate the device coordinates to body coordinates so that algorithms run by the medical device that use posture sensing can correct for the device orientation.

The calibration procedure involves determining the elements of a calibration matrix. Once the calibration matrix is determined, algorithms of the medical device can determine the posture of the patient such as by multiplying the output or outputs of the posture sensor by the calibration matrix to generate outputs calibrated to body coordinates. The calibrated outputs can be compared to specified thresholds to determine the posture.

In some examples, a three-dimensional DC accelerometer is used for the posture sensor. The accelerometer provides a DC-responsive output for each of three mutually orthogonal axes. To determine the elements of the calibration matrix, a coordinate rotation is performed. The Tait-Bryan angles can be used to define an arbitrary coordinate rotation.

Coordinate Transformation

Figure 5:
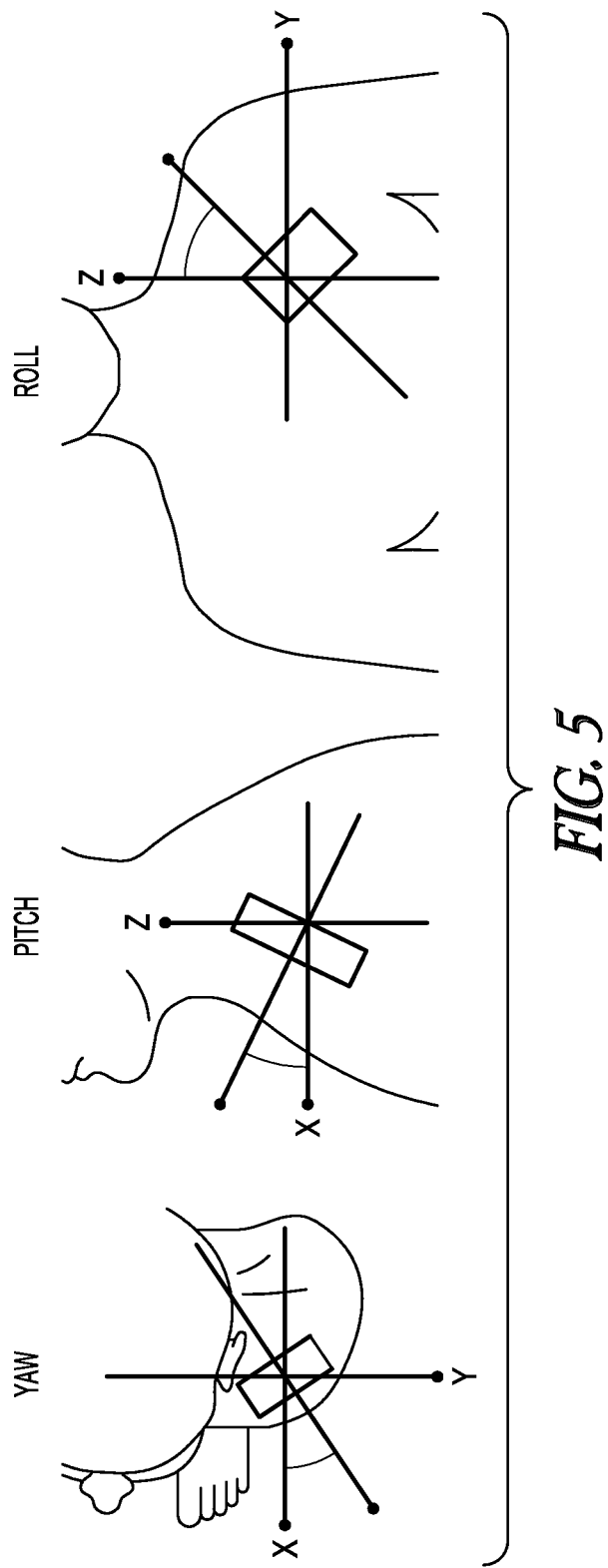
FIG. 5 illustrates the Tait-Bryan yaw, pitch, and roll angles and how they can be used to describe device coordinate to body coordinate rotations.

FIG. 5 shows the Tait-Bryan angles yaw, pitch, and roll and how they can be used to describe device coordinate to body coordinate rotations or transformations, such as for a pectorally implanted CFM device. The arbitrary coordinate rotation of the device on the body can be determined by three consecutive rotations. The first rotation can be about the inferior-superior (z) body axis or the vertical axis when the patient is upright. In FIG. 5 it can be seen that this angle can be the yaw angle, denoted as $\theta_y$.

If the device is mounted on the body with yaw angle $\theta_y$, any vector a originally expressed in body coordinates can be expressed in the rotated coordinate system as:

$$a' = \begin{bmatrix} a'_x \\ a'_y \\ a'_z \end{bmatrix} = \begin{bmatrix} \cos(\theta_y) & -\sin(\theta_y) & 0 \\ \sin(\theta_y) & \cos(\theta_y) & 0 \\ 0 & 0 & 1 \end{bmatrix} \begin{bmatrix} a_x \\ a_y \\ a_z \end{bmatrix}, \quad (1)$$

where a' represents the vector expressed in the coordinate system rotated through angle $\theta_y$ about the z axis.

This first rotation results in a new rotated y axis y'. The second rotation is about this y' axis, through an angle $\theta_p$ that can be referred to as the pitch angle:

$$a'' = \begin{bmatrix} a''_x \\ a''_y \\ a''_z \end{bmatrix} \quad (2)$$

$$= \begin{bmatrix} \cos(\theta_p) & 0 & \sin(\theta_p) \\ 0 & 1 & 0 \\ -\sin(\theta_p) & 0 & \cos(\theta_p) \end{bmatrix} \begin{bmatrix} a'_x \\ a'_y \\ a'_z \end{bmatrix}$$

$$= \begin{bmatrix} \cos(\theta_p) & 0 & -\sin(\theta_p) \\ 0 & 1 & 0 \\ \sin(\theta_p) & 0 & \cos(\theta_p) \end{bmatrix} \begin{bmatrix} \cos(\theta_y) & -\sin(\theta_y) & 0 \\ \sin(\theta_y) & \cos(\theta_y) & 0 \\ 0 & 0 & 1 \end{bmatrix} \begin{bmatrix} a_x \\ a_y \\ a_z \end{bmatrix}$$

where a" represents the vector expressed in the coordinate system rotated through angle $\theta_y$ about the z axis and then rotated through $\theta_p$ about the y' axis.

These two rotations result in a new rotated x axis x". The third rotation is about this x" axis, through an angle $\theta_r$ that can be referred to as the roll angle:

$$\begin{bmatrix} a'''_x \\ a'''_y \\ a'''_z \end{bmatrix} = \begin{bmatrix} 1 & 0 & 0 \\ 0 & \cos(\theta_r) & \sin(\theta_r) \\ 0 & -\sin(\theta_r) & \cos(\theta_r) \end{bmatrix} \begin{bmatrix} a''_x \\ a''_y \\ a''_z \end{bmatrix} \quad (3)$$

$$= \begin{bmatrix} 1 & 0 & 0 \\ 0 & \cos(\theta_r) & \sin(\theta_r) \\ 0 & -\sin(\theta_r) & \cos(\theta_r) \end{bmatrix} \begin{bmatrix} \cos(\theta_p) & 0 & \sin(\theta_p) \\ 0 & 1 & 0 \\ -\sin(\theta_p) & 0 & \cos(\theta_p) \end{bmatrix}$$

$$\begin{bmatrix} \cos(\theta_y) & -\sin(\theta_y) & 0 \\ \sin(\theta_y) & \cos(\theta_y) & 0 \\ 0 & 0 & 1 \end{bmatrix} \begin{bmatrix} a_x \\ a_y \\ a_z \end{bmatrix},$$

where a''' represents the vector expressed in the coordinate system rotated through angle $\theta_y$ about the z axis, rotated through $\theta_p$ about the y' axis, and then rotated through angle $\theta_r$ about the x" axis. The matrix on the right side of the equal sign can be multiplied out to yield:

$$\begin{bmatrix} a_u \\ a_v \\ a_w \end{bmatrix} = \begin{bmatrix} a'''_x \\ a'''_y \\ a'''_z \end{bmatrix} = \quad (4)$$

$$\begin{bmatrix} \cos(\theta_p)\cos(\theta_y) & -\cos(\theta_p)\sin(\theta_y) & \sin(\theta_p) \\ \cos(\theta_r)\sin(\theta_y) - \sin(\theta_r)\sin(\theta_p)\cos(\theta_y) & \cos(\theta_r)\cos(\theta_y) + \sin(\theta_r)\sin(\theta_p)\sin(\theta_y) & \sin(\theta_r)\cos(\theta_p) \\ -\sin(\theta_r)\sin(\theta_y) - \cos(\theta_r)\sin(\theta_p)\cos(\theta_y) & -\sin(\theta_r)\cos(\theta_y) + \cos(\theta_r)\sin(\theta_p)\sin(\theta_y) & \cos(\theta_r)\cos(\theta_p) \end{bmatrix}$$

$$\begin{bmatrix} a_x \\ a_y \\ a_z \end{bmatrix},$$

or $$\begin{bmatrix} a_u \\ a_v \\ a_w \end{bmatrix} = M \begin{bmatrix} a_x \\ a_y \\ a_z \end{bmatrix}, \quad (5)$$

where $a^T = [a_u \ a_v \ a_w]^T$ is the vector a expressed in the rotated coordinate system of the device.

Equation (4) can be used to calculate elements of the calibration matrix M for the posture sensor of the medical device. To determine the calibration matrix, a two posture manual calibration is performed. Additional postures (e.g., three) can be used, but two postures are sufficient. The subject assumes the first known posture and sensor data (e.g., acceleration data) is collected from the device which is mounted (e.g., implanted or worn) on the body. The subject then assumes a second posture and sensor data is collected while the subject is in the second posture. Calculations performed by the medical device on the sensor data collected from the two postures can be used to specify and correct for the orientation of the device in or on the body. These calculations need not involve trigonometric calculations. Non-trigonometric calculations can be useful on a device where processor power to perform the calculations is limited, or for a device where energy to perform processor calculations is limited (e.g., a battery powered device).

To construct the calibration matrix, a combination of direct insertion of sensor data and knowledge of the form of the calibration rotation matrix is used. A first sensor output for a first device axis is measured while the subject is in a first specified posture. In some examples, an upright posture is used and data $[a_u\ a_v\ a_w]^T$ is collected from the mounted device. For the upright posture, the gravity vector in body coordinates is $[a_u\ a_v\ a_w]^T = [0\ 0\ 1]^T$. The matrix equation for this situation is:

$$\begin{bmatrix} a_u \\ a_v \\ a_w \end{bmatrix}_{Upright} = \begin{bmatrix} \cos(\theta_p)\cos(\theta_y) & -\cos(\theta_p)\sin(\theta_y) & \sin(\theta_p) \\ -\cos(\theta_r)\sin(\theta_y) - \sin(\theta_r)\sin(\theta_p)\cos(\theta_y) & \cos(\theta_r)\cos(\theta_y) + \sin(\theta_r)\sin(\theta_p)\sin(\theta_y) & \sin(\theta_r)\cos(\theta_p) \\ -\sin(\theta_r)\sin(\theta_y) - \cos(\theta_r)\sin(\theta_p)\cos(\theta_y) & -\sin(\theta_r)\cos(\theta_y) + \cos(\theta_r)\sin(\theta_p)\sin(\theta_y) & \cos(\theta_r)\cos(\theta_p) \end{bmatrix} \begin{bmatrix} 0 \\ 0 \\ 1 \end{bmatrix}, \quad (6)$$

or $$\begin{bmatrix} a_u \\ a_v \\ a_w \end{bmatrix}_{Upright} = \begin{bmatrix} \sin(\theta_p) \\ \sin(\theta_r)\cos(\theta_p) \\ \cos(\theta_r)\cos(\theta_p) \end{bmatrix}. \quad (7)$$

If the components of the rotation matrix, M, are denoted as follows, $$M = \begin{bmatrix} m_{11} & m_{12} & m_{13} \\ m_{21} & m_{22} & m_{23} \\ m_{31} & m_{32} & m_{33} \end{bmatrix}, \quad (8)$$

then by inspection, $m_{13} = a_{u,Upright}$, $m_{23} = a_{v,Upright}$, $m_{33} = a_{w,Upright}$, where $a_{u,Upright}$ refers to the sensor output from the "u" device axis when the patient is in the upright position.

Pitch Angle (P) Coefficients

To calculate the calibration matrix elements associated with the pitch angle, it can be seen from the form of the matrix that $m_{13} = a_{u,Upright} = \sin(\theta_p)$. The term $a_{u,Upright}$ can be measured directly by the sensor with the patient in the Upright posture. If $\sin(\theta_p) = a_{u,Upright}$, then using the trigonometric identity $\cos(\theta_p) = \pm\sqrt{1-\sin^2(\theta_p)}$, $\cos(\theta_p)$ can be computed from the measured quantities $\cos(\theta_p) = \pm\sqrt{1-a_{u,Upright}^2}$.

Roll Angle (R) Coefficients

This expression for $\cos(\theta_p)$ can be used to calculate the calibration matrix elements associated with the roll angle. Two separate equations can be used to characterize the roll rotation: $\sin(\theta_r) = a_{v,Upright}/\pm\sqrt{1-a_{u,Upright}^2}$, and $\cos(\theta_r) = a_{w,Upright}/\pm\sqrt{1-a_{u,Upright}^2}$. Either of the equations can be used to calculate the roll rotation matrix components. However, due to one or both of inaccuracies in the patient maneuver and noise in the measurements during the maneuver, the results may not be identical in practice. Either of these equations can be used, or both of these equations can be used, to calculate the roll rotation matrix components to enhance the accuracy of the results.

To simplify the description, the notation for cosine and sine in the matrix above can be changed to:

$$\begin{bmatrix} a_u \\ a_v \\ a_w \end{bmatrix}_{Upright} = \begin{bmatrix} c_p c_y & -c_p s_y & s_p \\ c_r s_y - s_r s_p c_y & c_r c_y + s_r s_p s_y & s_r c_p \\ -s_r s_y - c_r s_p c_y & -s_r c_y + c_r s_p s_y & c_r c_p \end{bmatrix} \begin{bmatrix} 0 \\ 0 \\ 1 \end{bmatrix}, \quad (9)$$

where, e.g., $\cos(\theta_p)$ is equal to $c_p$. It can be seen that the nine components of the matrix are composed of the six coefficients $s_r, c_r, s_p, c_p$, and $s_y, c_y$. The "s" and "c" coefficients or matrix components are also related to one another as discussed previously.

The only trigonometric relationships needed are $s_i = \pm\sqrt{1-c_i^2}$, and $c_i = \pm\sqrt{1-s_i^2}$, for $i \in (y, p, r)$, which relate the components of matrix by algebraic equations. Thus, whenever we know a "c" term, we also know (within a sign ambiguity) the corresponding "s" term and vice-versa using algebraic expressions, and there is no need for trigonometric functions to compute the components of the matrix. Specifically, the equations are $$s_p = a_{u,Upright}$$

$$c_p = \pm\sqrt{1-s_p^2}$$

$$s_{ra} = a_{v,Upright}/c_p,\ c_{ra} = \pm\sqrt{1-s_{ra}^2},$$

$$c_{rb} = a_{w,Upright}/c_p,\ s_{rb} = \pm\sqrt{1-c_{rb}^2}, \quad (10)$$

where the additional "a" and "b" in the subscripts denote that these are two alternative sets of calculations that, as noted previously, may give different results in practice. Either the set "a" or the set "b" equations can be used. Note that $s_r, c_r$ should be calculated from the same set of equations so that $s_r$ and $c_r$ are calculated from complementary angles. This ensures that the rotation matrix is unitary (i.e., its inverse is equal to its transpose). Thus, by knowing $a_{u,Upright}$ and $a_{v,Upright}$, or knowing $a_{u,Upright}$ and $a_{w,Upright}$, four of the six coefficients can be calculated.

Yaw Angle (Y) Coefficients

Remaining to be computed are the two coefficients related to the yaw rotation, $s_y$ and $c_y$. In some examples, to determine this rotation, the patient assumes a second posture orthogonal to the first. For instance, the first position can be the upright posture and the second posture is the supine posture where the patient lies on his or her back. Similar to the upright posture, the gravity vector in body coordinates for the supine posture is $[a_u \ a_v \ a_w]^T = [1 \ 0 \ 0]^T$. This leads to the equation:

$$\begin{bmatrix} a_u \\ a_v \\ a_w \end{bmatrix}_{Supine} = \begin{bmatrix} c_p c_y & -c_p s_y & s_p \\ c_r s_y - s_r s_p c_y & c_r c_y + s_r s_p s_y & s_r c_p \\ -s_r s_y - c_r s_p c_y & -s_r c_y + c_r s_p s_y & c_r c_p \end{bmatrix} \begin{bmatrix} 1 \\ 0 \\ 0 \end{bmatrix}, \quad (11)$$

or $$\begin{bmatrix} a_u \\ a_v \\ a_w \end{bmatrix}_{Supine} = \begin{bmatrix} c_p c_y \\ c_r s_y - s_r s_p c_y \\ -s_r s_y - c_r s_p c_y \end{bmatrix}. \quad (12)$$

The simplest set of calculations for the yaw rotation coefficients is $c_y = a_{u,Supine}/c_p$, $s_y = \pm\sqrt{1-c_y^2}$, which again does not need to be computed using trigonometric functions. Thus, all six of the coefficients can be calculated using the outputs of the posture sensor, and therefore all nine elements of the calibration matrix M can be calculated. Thus, the calibration matrix can be calculated without actually calculating a rotation angle, such as one or more of a yaw, pitch, and roll angle, and can be calculated without calculating a trigonometric function.

When the calibration matrix M is calculated, the inverse of the calibration matrix $M^{-1}$ can be used to translate the posture sensor output in device coordinates to the posture sensor output in body coordinates, such as by $$\begin{bmatrix} a_x \\ a_y \\ a_z \end{bmatrix} = M^{-1} \begin{bmatrix} a_u \\ a_v \\ a_w \end{bmatrix}, \quad (13)$$

where $[a_u \ a_v \ a_w]$ is the output of the posture sensor in device coordinates and $[a_x \ a_y \ a_z]$ is the output of the posture sensor in body coordinates.

Alternate Coordinate Transformation

The examples of calibrating the device for orientation in or on the body has been described in regard to the patient first assuming an upright position and then assuming a supine position. Other calibration maneuvers can be useful, such as starting with the supine posture or with the patient lying on his or side. Sometimes it can be desirable to begin the calibration maneuvers from the supine posture and finish the calibration with the upright posture. This may be if calibration maneuvers starting from a fully upright posture are difficult to repeat. The maneuvers can be performed in either order. It is the choice of the order of the processing of the two maneuvers that allows choosing which maneuver needs to be fully aligned with gravity (that is, fully upright or fully supine).

To start from the supine position, the order of rotations used to calculate the calibration matrix are reversed. Because of the different order of the rotation, the rotation is not in the order of the Tait-Bryan formulation. This results in rotations that do not correspond directly to the roll, pitch, and yaw angles, but the roll, pitch, and yaw angles are still useful for describing the calculations of the elements of the calibration matrix.

As before, an arbitrary coordinate rotation of the device on the body can be determined by three consecutive rotations. The first rotation can be about the anterior-posterior (x) body axis. In FIG. 4 it can be seen that this angle is similar to the roll angle, and is denoted as $\theta_{r'}$.

If the device is mounted on the body with angle, $\theta_{r'}$, any vector, a, originally expressed in body coordinates can be expressed in the rotated coordinate system as:

$$a' = \begin{bmatrix} a'_x \\ a'_y \\ a'_z \end{bmatrix} = \begin{bmatrix} 1 & 0 & 0 \\ 0 & \cos(\theta_{r'}) & \sin(\theta_{r'}) \\ 0 & -\sin(\theta_{r'}) & \cos(\theta_{r'}) \end{bmatrix} \begin{bmatrix} a_x \\ a_y \\ a_z \end{bmatrix}, \quad (14)$$

where a' represents the vector expressed in the coordinate system rotated through angle $\theta_{r'}$ about the x axis.

This first rotation results in a new rotated y axis y'. The second rotation is about this y' axis, through an angle $\theta_{p'}$ which for small roll angles is an angle similar to the pitch angle:

$$a'' = \begin{bmatrix} a''_x \\ a''_y \\ a''_z \end{bmatrix} \quad (15)$$

$$= \begin{bmatrix} \cos(\theta_{p'}) & 0 & \sin(\theta_{p'}) \\ 0 & 1 & 0 \\ -\sin(\theta_{p'}) & 0 & \cos(\theta_{p'}) \end{bmatrix} \begin{bmatrix} a'_x \\ a'_y \\ a'_z \end{bmatrix}$$

$$= \begin{bmatrix} \cos(\theta_{p'}) & 0 & \sin(\theta_{p'}) \\ 0 & 1 & 0 \\ -\sin(\theta_{p'}) & 0 & \cos(\theta_{p'}) \end{bmatrix} \begin{bmatrix} 1 & 0 & 0 \\ 0 & \cos(\theta_{r'}) & \sin(\theta_{r'}) \\ 0 & -\sin(\theta_{r'}) & \cos(\theta_{r'}) \end{bmatrix} \begin{bmatrix} a_x \\ a_y \\ a_z \end{bmatrix}$$

where a" represents the vector expressed in the coordinate system rotated through angle $\theta_{r'}$ about the x axis and then rotated through $\theta_{p'}$ about the y' axis.

These two rotations result in a new rotated z axis z". The third rotation is about this z" axis, through an angle $\theta_{y'}$, which for small roll angles is an angle similar to the yaw angle.

$$\begin{bmatrix} a'''_x \\ a'''_y \\ a'''_z \end{bmatrix} = \begin{bmatrix} \cos(\theta_{y'}) & -\sin(\theta_{y'}) & 0 \\ \sin(\theta_{y'}) & \cos(\theta_{y'}) & 0 \\ 0 & 0 & 1 \end{bmatrix} \begin{bmatrix} a''_x \\ a''_y \\ a''_z \end{bmatrix} \quad (16)$$

$$= \begin{bmatrix} \cos(\theta_{y'}) & -\sin(\theta_{y'}) & 0 \\ \sin(\theta_{y'}) & \cos(\theta_{y'}) & 0 \\ 0 & 0 & 1 \end{bmatrix} \begin{bmatrix} \cos(\theta_{p'}) & 0 & \sin(\theta_{p'}) \\ 0 & 1 & 0 \\ -\sin(\theta_{p'}) & 0 & \cos(\theta_{p'}) \end{bmatrix}$$

$$\begin{bmatrix} 1 & 0 & 0 \\ 0 & \cos(\theta_{r'}) & \sin(\theta_{r'}) \\ 0 & -\sin(\theta_{r'}) & \cos(\theta_{r'}) \end{bmatrix} \begin{bmatrix} a_x \\ a_y \\ a_z \end{bmatrix},$$

where $a''' = [a'''_x \ a'''_y \ a'''_z]$ represents the vector expressed in the coordinate system rotated through angle $\theta'_{r'}$ about the x axis, rotated through $\theta_{p'}$ about the y' axis, and then rotated through angle $\theta_{y'}$ about the z" axis. The matrix on the right side of the equal sign can be multiplied out to yield:

$$\begin{bmatrix} a_u \\ a_v \\ a_w \end{bmatrix} = \begin{bmatrix} a_x''' \\ a_y''' \\ a_z''' \end{bmatrix} \quad (17)$$

$$= \begin{bmatrix} \cos(\theta_{y'})\cos(\theta_{p'}) & -\sin(\theta_{y'})\cos(\theta_{r'}) - \cos(\theta_{y'})\sin(\theta_{p'}) & -\sin(\theta_{r'})\sin(\theta_{y'}) + \cos(\theta_{r'})\sin(\theta_{p'}) \\ \sin(\theta_{y'})\cos(\theta_{p'}) & \cos(\theta_{r'})\cos(\theta_{y}) - \sin(\theta_{r})\sin(\theta_{p'}) & \sin(\theta_{r'})\cos(\theta_{y'}) + \sin(\theta_{y})\sin(\theta_{p}) \\ -\sin(\theta_{p'}) & \sin(\theta_{r'}) & \cos(\theta_{y'}) \\ -\sin(\theta_{p'}) & -\cos(\theta_{p'})\sin(\theta_{r'}) & \cos(\theta_{p})\cos(\theta_{r'}) \end{bmatrix} \begin{bmatrix} a_x \\ a_y \\ a_z \end{bmatrix},$$

or $$\begin{bmatrix} a_u \\ a_v \\ a_w \end{bmatrix} = M \begin{bmatrix} a_x \\ a_y \\ a_z \end{bmatrix}, \quad (18)$$

where $a^T = [a_u \ a_v \ a_w]^T$ is the vector a expressed in the device coordinates.

A two posture manual calibration is again performed to determine the calibration matrix. The subject first assumes the supine posture and sensor data $[a_u \ a_v \ a_w]^T$ is collected from the mounted device. The subject then assumes a second posture and sensor data is collected while the subject is in the second posture. For the supine posture, the gravity vector in body coordinates is $[a_u \ a_v \ a_w]^T = [1 \ 0 \ 0]^T$. The matrix equation for this situation is:

$$\begin{bmatrix} a_u \\ a_v \\ a_w \end{bmatrix}_{Supine} = \begin{bmatrix} \cos(\theta_{y'})\cos(\theta_{p'}) & -\sin(\theta_{y'})\cos(\theta_{r'}) - \cos(\theta_{y'})\sin(\theta_{p'}) & -\sin(\theta_{r'})\sin(\theta_{y'}) + \cos(\theta_{r'})\sin(\theta_{p'}) \\ \sin(\theta_{y'})\cos(\theta_{p'}) & \cos(\theta_{r})\cos(\theta_{y}) - \sin(\theta_{r})\sin(\theta_{p'}) & \sin(\theta_{r'})\cos(\theta_{y}) + \sin(\theta_{y'})\sin(\theta_{p'}) \\ & \sin(\theta_{y'}) & \cos(\theta_{r'}) \\ -\sin(\theta_{p'}) & -\cos(\theta_{p'})\sin(\theta_{r'}) & \cos(\theta_{p'})\cos(\theta_{r'}) \end{bmatrix} \begin{bmatrix} 1 \\ 0 \\ 0 \end{bmatrix}, \quad (19)$$

or $$\begin{bmatrix} a_u \\ a_v \\ a_w \end{bmatrix}_{Supine} = \begin{bmatrix} \cos(\theta_{y'})\cos(\theta_{p'}) \\ \sin(\theta_{y'})\cos(\theta_{p'}) \\ -\sin(\theta_{p'}) \end{bmatrix}. \quad (20)$$

The components of the rotation matrix, M, are denoted as follows, $$M = \begin{bmatrix} m_{11} & m_{12} & m_{13} \\ m_{21} & m_{22} & m_{23} \\ m_{31} & m_{32} & m_{33} \end{bmatrix}, \quad (21)$$

and by inspection $m_{11} = a_{u, Supine}$, $m_{21} = a_{v, Supine}$, $m_{31} = a_{w, Supine}$, where $a_{u, Supine}$ refers to the sensor output from the "u" device axis when the patient is in the supine position.

P' Angle Coefficients

To calculate the calibration matrix elements associated with $\theta_{p'}$, it can be seen from the form of the matrix that $m_{31} = -\sin(\theta_{p'})$, so that $\sin(\theta_{p'}) = -a_{w, Supine}$. The term $a_{w, Supine}$ can be measured directly by the sensor with the patient in the Supine posture. If $\sin(\theta_{p'}) = -a_{w, Supine}$, then using the trigonometric identity $\cos(\theta_{p'}) = \pm\sqrt{1 - \sin^2(\theta_{p'})}$, $\cos(\theta_{p'})$ can be computed from the measured quantities $\cos(\theta_{p'}) = a_{w, Supine}^2$.

Y' Angle Coefficients

This expression for $\cos(\theta_{p'})$ can be used to calculate the calibration matrix elements associated with $\theta_{y'}$. Two separate equations that can be used to characterize the roll rotation are: $\sin(\theta_{y'}) = a_{v, Supine}/\pm\sqrt{1 - a_{w, Supine}^2}$, and $\cos(\theta_{y'}) = a_{u, Supine}/\pm\sqrt{1 - a_{w, Supine}^2}$. As before, either of the equations can be used to calculate the roll rotation matrix components but the results may not be identical in practice. Both of these equations can be used to calculate the $\theta_{y'}$ rotation matrix components to enhance the accuracy of the results.

Again, simplifying the notation leads to the equation:

$$\begin{bmatrix} a_u \\ a_v \\ a_w \end{bmatrix}_{Supine} = \begin{bmatrix} c_p c_y & -c_r s_y - s_r s_p c_y & -s_r s_y + c_r s_p c_y \\ c_p s_y & c_r c_y - s_r s_p s_y & c_y s_r + c_r s_p s_y \\ -s_p & -s_r c_p & c_r c_p \end{bmatrix} \begin{bmatrix} 1 \\ 0 \\ 0 \end{bmatrix}. \quad (22)$$

In simplified notation, the non-trigonometric equations are:

$$s_p = -a_{w, Supine}$$

$$c_p = \pm\sqrt{1 - s_p^2},$$

$$s_{ya} = a_{v, Supine}/c_p, \ c_{ya} = \pm\sqrt{1 - s_{ya}^2},$$

$$c_{yb} = a_{u, Supine}/c_p, \ s_{yb} = \pm\sqrt{1 - c_{yb}^2}, \quad (23)$$

where the additional "a" and "b" in the subscripts denote that these are two alternative sets of calculations may give different results in practice. Either the set "a" or the set "b" equations should be used and $s_y$, $c_y$ calculated from the same set of equations. Thus, by knowing $a_{w, Supine}$ and $a_{v, Supine}$, or knowing $a_{w, Supine}$ and $a_{u, Supine}$, four of the six coefficients can be calculated.

R' Angle Coefficients

Remaining to be computed are the two coefficients related to $\theta_{r'}$; namely $s_r$ and $c_r$. In some examples, to determine this rotation, the patient assumes an upright posture (e.g., standing). The gravity vector in body coordinates for the upright posture is $[a_u \ a_v \ a_w]^T = [0 \ 0 \ 1]^T$. This leads to the equation:

$$\begin{bmatrix} a_u \\ a_v \\ a_w \end{bmatrix}_{Upright} = \begin{bmatrix} c_p c_y & -c_r s_y - s_r s_p c_y & -s_r s_y + c_r s_p c_y \\ c_p s_y & c_r c_y - s_r s_p s_y & c_y s_r + c_r s_p s_y \\ -s_p & -s_r c_p & c_r c_p \end{bmatrix} \begin{bmatrix} 0 \\ 0 \\ 1 \end{bmatrix}, \quad (24)$$

or $$\begin{bmatrix} a_u \\ a_v \\ a_w \end{bmatrix}_{Upright} = \begin{bmatrix} -s_r s_y + c_r s_p c_y \\ c_y s_r + c_r s_p s_y \\ c_r c_p \end{bmatrix}. \quad (25)$$

The simplest set of calculations for the $\theta_{r'}$ coefficients is $c_r = a_{w, Upright}/c_p$, $s_r = \pm\sqrt{1 - c_r^2}$. All six of the coefficients can be calculated and therefore all nine elements of the calibration matrix M can be calculated. As with the first example where the subject is first upright and is supine second, the elements of the calibration matrix are calculated without using a trigonometric function and without expressly calculating an orientation angle.

Figure 6:
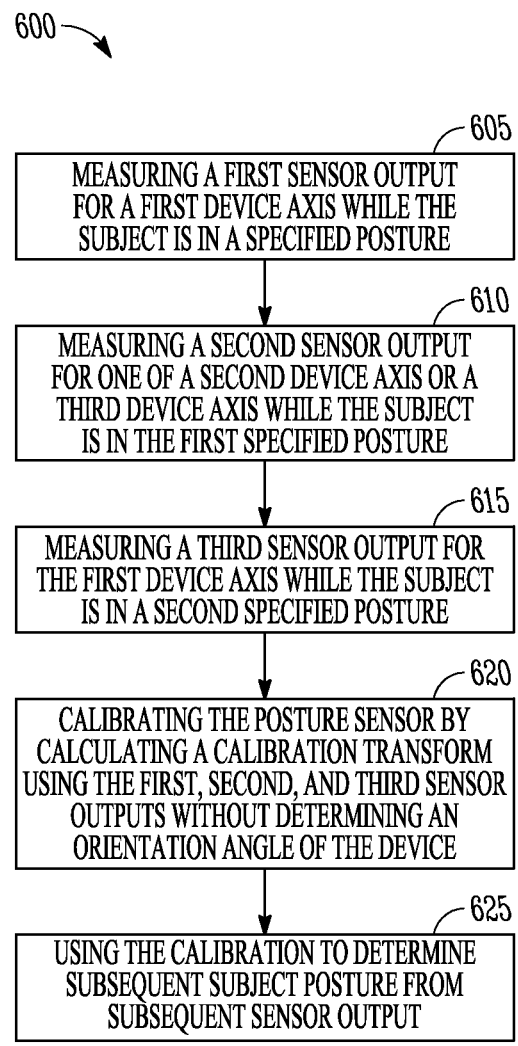
FIG. 6 is a flow diagram of a method of determining a calibration matrix for a multi-dimensional posture sensor.

FIG. 6 is a flow diagram of a method 600 of determining a calibration matrix for a multi-dimensional posture sensor. At block 605, a first sensor output is measured for a first device axis while the subject is in a first specified posture. The first device axis can be the u axis, v axis, or w axis. In some examples, the first specified posture is the upright posture and the first sensor output can be $a_{u,Upright}$. In some examples, the first specified posture is the supine posture and the first sensor output can be $a_{w,\,Supine}$. Other postures (e.g., lying on one's side) can be used for the first posture.

At block 610, a second sensor output is measured for one of a second device axis or a third device axis while the subject is in the first specified posture. In some examples, the first sensor output can be $a_{u,Upright}$ and the second sensor output can be $a_{v,Upright}$ or $a_{w,Upright}$. In some examples, the first sensor output can be $a_{w,\,Supine}$ and the second sensor output can be $a_{v,\,Supine}$ or $a_{u,\,Supine}$. In certain examples, a sensor output is measured for both the second device axis and the third device axis.

At block 615, at least a third sensor output is measured for the first device axis while the subject is in a second specified posture. The second specified posture can be orthogonal to the first specified posture. As an example, the first sensor output can be $a_{u,Upright}$ and the third sensor output can be $a_{u,\,Supine}$. In another example, the first sensor output can be $a_{w,\,Supine}$ and the third can be $a_{w,Upright}$.

At block 620, the posture sensor is calibrated by calculating a calibration transform using the first, second, and third sensor outputs without determining an orientation angle of the device. In some examples, elements of a matrix to calibrate the posture sensor are calculated using the first, second, and third sensor outputs. For example, components of the elements can be calculated using the algebraic (and non-trigonometric) equations:

$$s_p = a_{u,Upright}$$

$$c_p = \pm\sqrt{1-s_p^2}$$

$$s_{ra} = a_{v,Upright}/c_p, \quad c_{ra} = \pm\sqrt{1-s_{ra}^2},$$

$$c_{rb} = a_{w,Upright}/c_p, \quad s_{rb} = \pm\sqrt{1-c_{rb}^2},$$

$$c_y = a_{u,Supine}/c_p,$$

$$s_y = \pm\sqrt{1-c_y^2}, \quad (26)$$

without expressly calculating any of the orientation angles $\theta_p$, $\theta_r$, or $\theta_y$. The first set of matrix components $s_p$, $c_p$, is related to a first orientation angle $\theta_p$, and are calculated using the first sensor output $a_{u,Upright}$. The second set of matrix components $s_r$, $c_r$, is related to a second orientation angle $\theta_r$, and are calculated using the first sensor output $a_{u,Upright}$ (from $s_p$, $c_p$), and a second sensor output; either $a_{v,Upright}$ or $a_{w,Upright}$. The third set of matrix components $s_y$, $c_y$, is related to a third orientation angle $\theta_y$, and is calculated using a third sensor output $a_{u,\,Supine}$. The matrix components $s_p$, $c_p$, $s_r$, $c_r$, $s_y$, and $c_y$ are then used to calculate the matrix elements of the calibration matrix M.

In another example, the matrix elements can be calculated using the algebraic equations:

$$s_p = -a_{w,Supine}$$

$$c_p = \pm\sqrt{1-s_p^2}$$

$$s_{ya} = a_{v,Supine}/c_p, \quad c_{ya} = \pm\sqrt{1-s_{ya}^2},$$

$$c_{yb} = a_{u,Supine}/c_p, s_{yb} = \pm\sqrt{1-c_{yb}^2},$$

$$c_r = a_{w,Upright}/c_p,$$

$$s_r = \pm\sqrt{1-c_r^2}, \quad (27)$$

without expressly calculating any of the orientation angles $\theta_p$, $\theta_r$, or $\theta_y$.

At block 625, the calibration can be used to determine subsequent subject posture from subsequent sensor output. In some examples, a calibration matrix is used to determine the posture. In some examples, the output of the posture sensor is compared to one or more thresholds to determine the posture or approximate posture of the subject.

If the posture sensor is a multi-dimensional posture sensor where the axes are aligned with the body axes, the outputs of the posture sensor would be $[a_u\ a_v\ a_w]=[1\ 0\ 0]$ in body coordinates when the subject is upright and would be $[a_u\ a_v\ a_w]=[0\ 0\ 1]$ when the subject is supine. However, the outputs will differ from these values when the device coordinates are different from the body coordinates.

The output of the multi-dimensional posture sensor can be viewed as a vector (e.g., a g vector). To transform the sensor outputs from device coordinates to body coordinates, the sensor output, or g vector, is multiplied by the calibration matrix. For instance, if $a_u$, $a_v$, $a_w$, are the sensor outputs for each of three orthogonal axes of the multi-dimensional sensor in device coordinates and M is the calibration matrix, then $$\begin{bmatrix} a_x \\ a_y \\ a_z \end{bmatrix} = M^{-1} \begin{bmatrix} a_u \\ a_v \\ a_w \end{bmatrix}, \quad (28)$$

where $a_x$, $a_y$, $a_z$ are the corresponding sensor measurements, or g vector, in the body coordinate system. The converted or transformed sensor outputs $a_x$, $a_y$, $a_z$ are compared to specified thresholds (e.g., programmed into a medical device) to determine posture.

In some examples, one or more angles are calculated from the transformed sensor outputs. The calculated angles are compared to specified threshold angles to determine patient posture. An approach for determining patient posture from a calibrated multi-dimensional posture sensor can be found in Wang et al., "Posture Detector Calibration and Use," U.S. Patent Pub. No. US 2007/0118056, filed Nov. 18, 2005, which is incorporated herein by reference in its entirety.

Non-orthogonal Calibration Maneuvers

Sometimes having to use mutually orthogonal postures is not desirable. In some situations it may not be advisable to place the patient in a fully recumbent or supine posture, such as when the patient has orthopnea and lying flat is difficult. This can make calibration of the sensor difficult to perform. In some situations it may be difficult for the patient to remain perfectly still while being perfectly upright. This can lead to inaccuracy in the calibration. Thus, it would be desirable to have expressions for components of the elements of the calibration matrix that don't require two mutually orthogonal postures for calibration.

Alternative Calculations for the Yaw Angle (Y) Coefficients

For the examples where the calibration maneuver includes the patient first in an upright posture and second in a supine posture, the same expressions are used for the pitch and roll components $s_p$, $c_p$, $s_r$, and $c_r$, but different expressions are used for the yaw components, $s_y$ and $c_y$, that allow the patient to be in a second posture that is more supine than the upright posture but is less than fully supine.

Rewriting Equation (3) in the simplified notation yields:

$$\begin{bmatrix} a_u \\ a_v \\ a_w \end{bmatrix} = M \begin{bmatrix} a_x \\ a_y \\ a_z \end{bmatrix} \quad (29)$$

$$= M_r M_p M_y \begin{bmatrix} a_x \\ a_y \\ a_z \end{bmatrix}$$

$$= \begin{bmatrix} 1 & 0 & 0 \\ 0 & c_r & s_r \\ 0 & -s_r & c_r \end{bmatrix} \begin{bmatrix} c_p & 0 & s_p \\ 0 & 1 & 0 \\ -s_p & 0 & c_p \end{bmatrix} \begin{bmatrix} c_y & -s_y & 0 \\ s_y & c_y & 0 \\ 0 & 0 & 1 \end{bmatrix} \begin{bmatrix} a_x \\ a_y \\ a_z \end{bmatrix}.$$

The inverse of the matrix M ($M^1$) is calculated to rotate back from device toward body coordinates. The inverse of the product of matrices is the product of the inverses of the matrices in reversed (left-to-right) order. Also, because the use of the "s" and "c" values are consistent, the individual rotation matrices are unitary, and the inverses of the rotation matrices are equal to the transposes of the matrices. Thus, fully rotating from body to device coordinates involves $$\begin{bmatrix} a_x \\ a_y \\ a_z \end{bmatrix} = M^{-1} \begin{bmatrix} a_u \\ a_v \\ a_w \end{bmatrix} \quad (30)$$

$$= M_y^{-1} M_p^{-1} M_r^{-1} \begin{bmatrix} a_u \\ a_v \\ a_w \end{bmatrix}$$

$$= \begin{bmatrix} c_y & s_y & 0 \\ -s_y & c_y & 0 \\ 0 & 0 & 1 \end{bmatrix} \begin{bmatrix} c_p & 0 & -s_p \\ 0 & 1 & 0 \\ s_p & 0 & c_p \end{bmatrix} \begin{bmatrix} 1 & 0 & 0 \\ 0 & c_r & -s_r \\ 0 & s_r & c_r \end{bmatrix} \begin{bmatrix} a_u \\ a_v \\ a_w \end{bmatrix}.$$

The first two (right-most) rotations or transformations on $[a_u\ a_v\ a_w]^T$ result in $$\begin{bmatrix} a'_x \\ a'_y \\ a'_z \end{bmatrix} == M_p^{-1} M_r^{-1} \begin{bmatrix} a_u \\ a_v \\ a_w \end{bmatrix} \quad (31)$$

$$= \begin{bmatrix} c_p & 0 & -s_p \\ 0 & 1 & 0 \\ s_p & 0 & c_p \end{bmatrix} \begin{bmatrix} 1 & 0 & 0 \\ 0 & c_r & -s_r \\ 0 & s_r & c_r \end{bmatrix} \begin{bmatrix} a_u \\ a_v \\ a_w \end{bmatrix}.$$

In this coordinate system, the z' axis is aligned with the body's inferior-superior (z) axis, and it merely remains to rotate about the z' axis to align the x' and y' axes with the x and y axes, respectively. If the patient reclines straight back (e.g., not tilting to either side but not necessarily fully supine), then there will be a projection of the gravity vector perpendicular to the z' axis, that is in the (x', y') plane.

Figure 7:
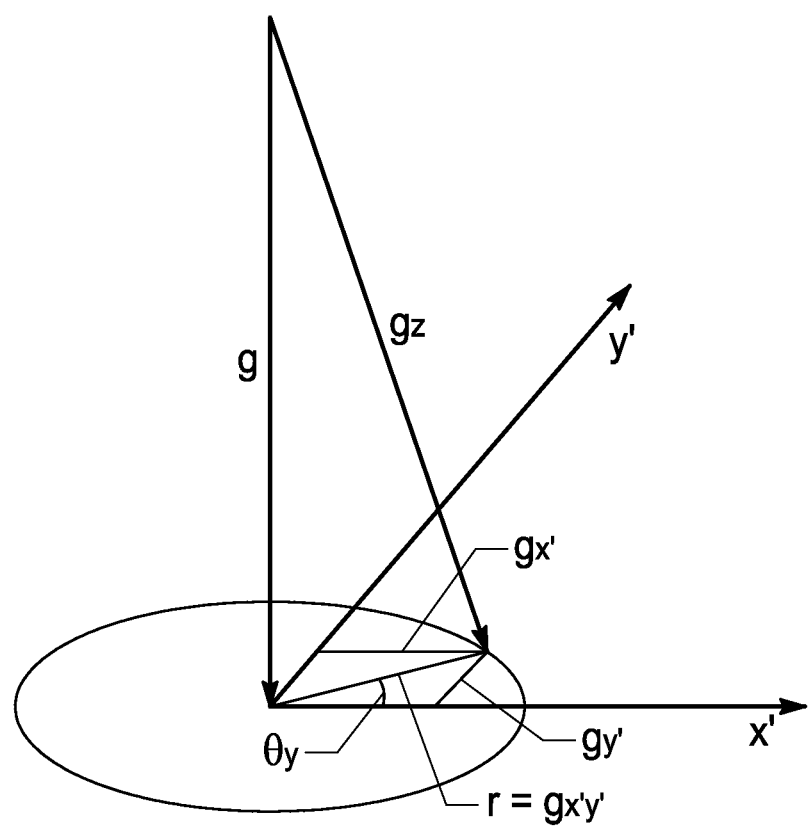
FIG. 7 graphically illustrates a component of the g force that is in the (x', y') plane to visualize transforming from device coordinates toward body coordinates.

FIG. 7 graphically shows the component of the g force that is in the (x', y') plane as radius r. It can be seen from the triangles in the Figure that the yaw components $s_y$ and $c_y$ can be computed from the x' and y' components as follows:

$$r = \sqrt{a'^2_x + a'^2_y},$$

$$c_y = a'_x / r$$

$$s_y = a'_y / r. \quad (32)$$

To calculate $s_y$ and $c_y$, the outputs of the posture sensor for the supine position $a_{u,Supine}$, $a_{v,Supine}$, $a_{w,Supine}$ are multiplied by the rotation matrices in the equation above to obtain $a_y'$, $a_y'$, and $a_z'$. The transformed outputs $a_y'$, $a_y'$, and $a_z'$ are then used to calculate $s_y$ and $c_y$. Note that in the previous calibration method $a_{u,Supine}$ is already measured. Thus, only two additional measurements are needed $a_{v,Supine}$ and $a_{w,Supine}$ in this calibration method.

Alternative Calculations for the R' Angle Coefficients

If it is desired to calibrate by placing the patient first in a supine posture and second in an upright posture, the same expressions are used for the yaw and pitch components $s_y$, $c_y$, $s_p$, and $c_p$, but different expressions are used for the roll components, $s_r$ and $c_r$, that allow the patient to be in a second posture that is more upright than the supine posture but is less than fully upright.

Rewriting the Equation (16) in the simplified notation yields:

$$\begin{bmatrix} a_u \\ a_v \\ a_w \end{bmatrix} = M \begin{bmatrix} a_x \\ a_y \\ a_z \end{bmatrix} \quad (33)$$

$$= M_y M_p M_r \begin{bmatrix} a_x \\ a_y \\ a_z \end{bmatrix}$$

$$= \begin{bmatrix} c_y & -s_y & 0 \\ s_y & c_y & 0 \\ 0 & 0 & 1 \end{bmatrix} \begin{bmatrix} c_p & 0 & s_p \\ 0 & 1 & 0 \\ -s_p & 0 & c_p \end{bmatrix} \begin{bmatrix} 1 & 0 & 0 \\ 0 & c_r & s_r \\ 0 & -s_r & c_r \end{bmatrix} \begin{bmatrix} a_x \\ a_y \\ a_z \end{bmatrix}.$$

The matrix inverse $M^1$ is calculated to rotate back from device toward body coordinates. As before, because the inverse of the product of matrices is the product of the inverses of the matrices in reversed (left-to-right) order, and because the inverses of the rotation matrices are equal to the transposes of the matrices, rotating from body to device coordinates involves $$\begin{bmatrix} a_x \\ a_y \\ a_z \end{bmatrix} = M^{-1} \begin{bmatrix} a_u \\ a_v \\ a_w \end{bmatrix} \quad (34)$$

$$= M_r^{-1} M_p^{-1} M_y^{-1} \begin{bmatrix} a_u \\ a_v \\ a_w \end{bmatrix}$$

$$= \begin{bmatrix} 1 & 0 & 0 \\ 0 & c_r & -s_r \\ 0 & s_r & c_r \end{bmatrix} \begin{bmatrix} c_p & 0 & -s_p \\ 0 & 1 & 0 \\ s_p & 0 & c_p \end{bmatrix} \begin{bmatrix} c_y & s_y & 0 \\ -s_y & c_y & 0 \\ 0 & 0 & 1 \end{bmatrix} \begin{bmatrix} a_u \\ a_v \\ a_w \end{bmatrix}.$$

The first two (right-most) rotations on $[a_u, a_v\ a_w]^T$ result in $$\begin{bmatrix} a'_x \\ a'_y \\ a'_z \end{bmatrix} == M_p^{-1} M_y^{-1} \begin{bmatrix} a_u \\ a_v \\ a_w \end{bmatrix} \quad (35)$$

$$= \begin{bmatrix} c_p & 0 & -s_p \\ 0 & 1 & 0 \\ s_p & 0 & c_p \end{bmatrix} \begin{bmatrix} c_y & -s_y & 0 \\ s_y & c_y & 0 \\ 0 & 0 & 1 \end{bmatrix} \begin{bmatrix} a_u \\ a_v \\ a_w \end{bmatrix}.$$

This time, the x' axis is aligned with the body's anterior-posterior (x) axis, and it merely remains to rotate about the x' axis to align the y' and z' axes with the y and z axes, respectively. If the patient is mostly upright (e.g., not tilting to either side but not necessarily fully upright), then there will be a projection of the gravity vector perpendicular to the x' (x) axis, that is in the (y', z') plane.

Figure 8:
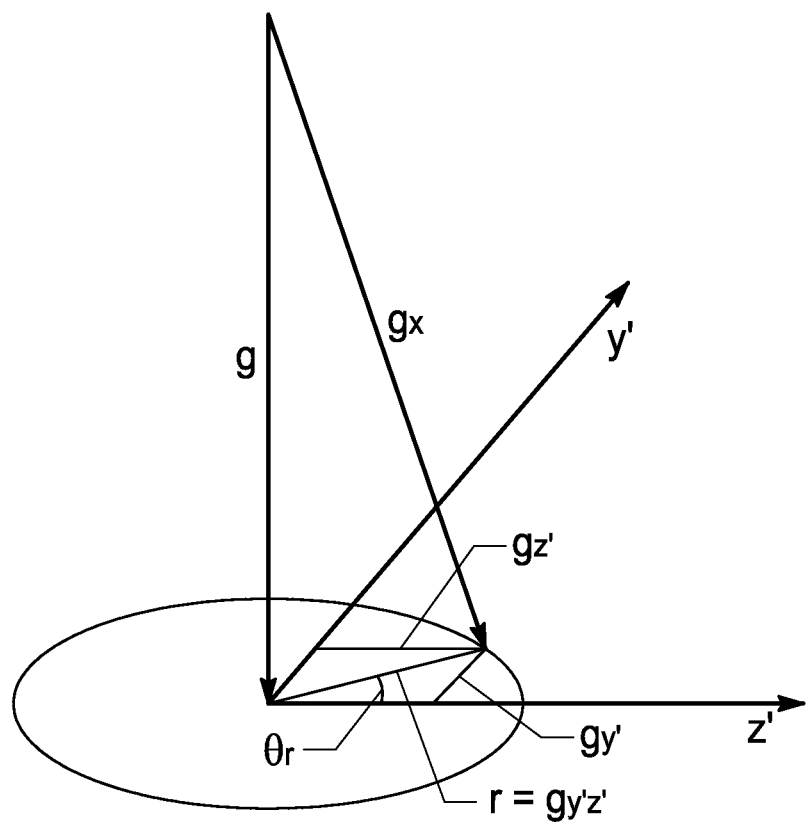
FIG. 8 graphically illustrates a component of the g force that is in the (y', z') plane to visualize transforming from device coordinates toward body coordinates.

FIG. 8 graphically shows the component of the g force that is in the (y', z') plane as radius r. It can be seen from the triangles in the Figure that the yaw components $s_r$ and $c_r$ can be computed from the x' and z' components as follows:

$$r=\sqrt{a_y'^2+a_z'^2},$$

$$s_r=a_y'/r,$$

$$c_r=a_z'/r \quad (36)$$

To calculate $s_r$ and $c_r$, the outputs of the posture sensor for the supine position right $a_{u,Upright}$, $a_{v,Upright}$, $a_{w,Upright}$, are multiplied by the rotation matrices in the equation above to obtain $a_x'$, $a_y'$, and $a_z'$. The transformed outputs $a_x'$, $a_y'$, and $a_z'$ are then used to calculate $s_r$ and $c_r$. As in the alternate Yaw angle example, two additional measurements are needed $a_{v,Upright}$ and $a_{w,Upright}$ in this calibration method.

Figure 9:
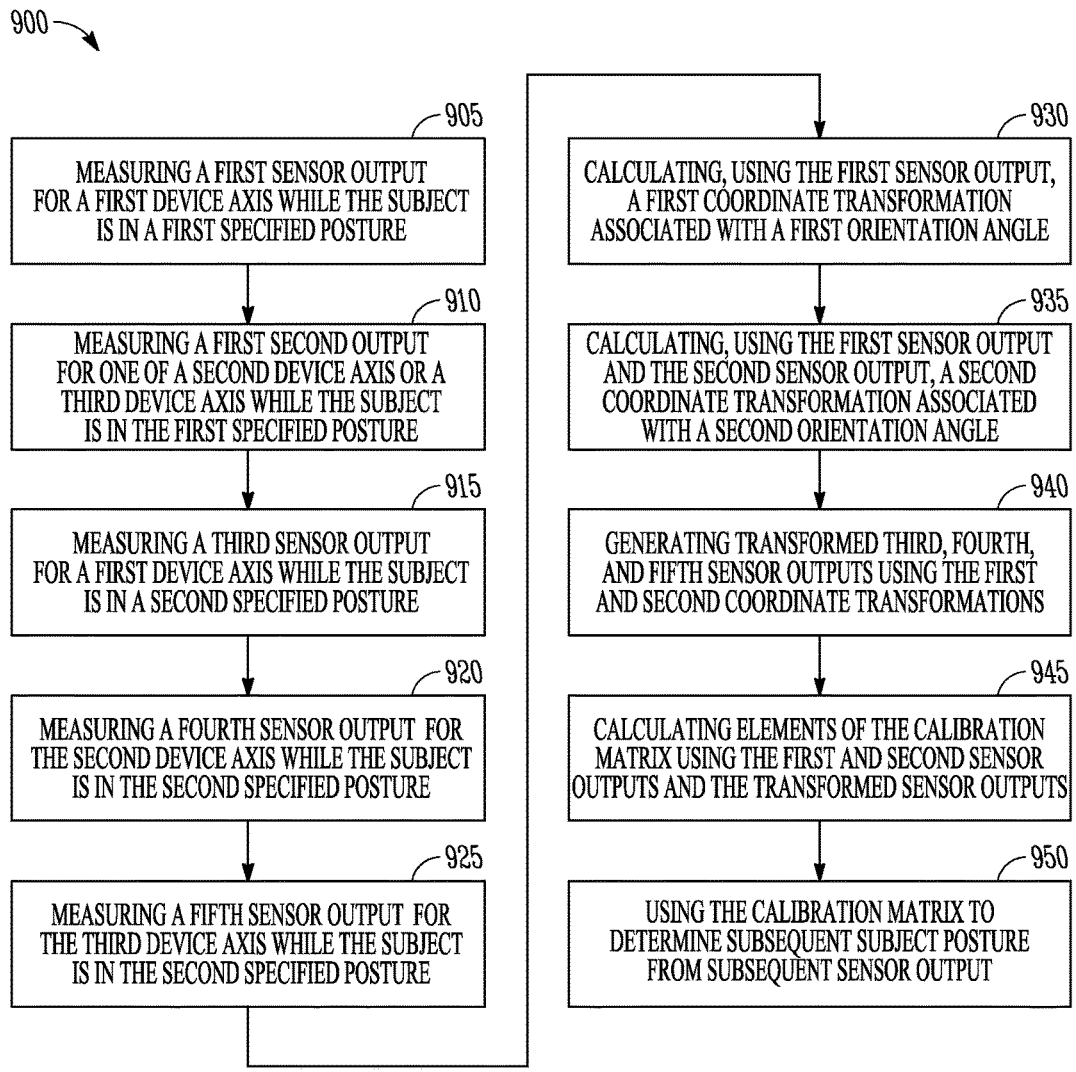
FIG. 9 is a flow diagram of another method of determining a calibration matrix for a multi-dimensional posture sensor.

FIG. 9 is a flow diagram of another method 900 of determining a calibration matrix for a multi-dimensional posture sensor. Similar to the method 600 of FIG. 6, at block 905, a first sensor output is measured for a first device axis while the subject is in a first specified posture. In some examples, the first specified posture is the upright posture and the first sensor output can be $a_{u,Upright}$. In some examples, the first specified posture is the supine posture and the first sensor output can be $a_{w, Supine}$. Other postures (e.g., lying on one's side) can be used for the first posture.

At block 910, a second sensor output is measured for one of a second device axis or a third device axis while the subject is in the first specified posture. In some examples, the first sensor output can be $a_{u,Upright}$ and the second sensor output can be $a_{v,Upright}$ or $a_{w,Upright}$. In some examples, the first sensor output can be $a_{w, Supine}$ and the second sensor output can be $a_{v, Supine}$ or $a_{u, Supine}$. In certain examples, a sensor output is measured for both the second device axis and the third device axis.

At block 915, a third sensor output is measured for the first device axis while the subject is in a second specified posture. The second specified posture can be non-orthogonal to the first specified posture. As an example, the first posture can be the upright posture, the first sensor output can be $a_{u,Upright}$, the second specified posture can be more supine than the first posture and less than fully supine, and the third sensor output may be $a_{u, less\ than\ Supine}$. In another example, the first specified posture can be the supine posture, the first sensor output may be $a_{w, Supine}$, the second posture can be more upright than the first posture and less than fully upright, and the third sensor output may be $a_{w, less\ than\ Upright}$.

At block 920, a fourth sensor output for the second device axis is measured while the subject is in the second specified posture. In some examples, the fourth sensor output may be $a_{v, less\ than\ Supine}$. In some examples, the fourth sensor output may be $a_{v, less\ than\ Upright}$.

At block 925, a fifth sensor output for the third device axis measured while the subject is in the second specified posture. In some examples, the fifth sensor output may be $a_{w, less\ than\ supine}$. In some examples, the fifth sensor output may be $a_{u, less\ than\ Upright}$.

At block 930, a first coordinate transformation associated with a first orientation angle is calculated, and at block 935, a second coordinate transformation associated with a second orientation angle is calculated using the first sensor output and the second sensor output. In some examples, the first and second transformations include the two (right-most) rotations on $[a_u\ a_v\ a_w]^T$ in equations (30) or (34).

At block 940, transformed third, fourth, and fifth sensor outputs are generated using the first and second coordinate transformations. In some examples, transformed sensor outputs $a_x'$, $a_y'$, and $a_z'$ are generated from sensor outputs $a_u$, $a_v$, $a_w$, using the rotations as in equation (31) or in equation (35).

At block 945, elements of the calibration matrix are calculated using the first and second sensor outputs and the transformed sensor outputs. In some examples, the first posture maneuver is upright and the second maneuver is less than fully supine and the elements of the calibration matrix are calculated using $s_p$, $c_p$, $s_r$, and $c_r$ using equations (26), and using $s_y$, $c_y$ using the equations (32). In some examples, the first posture maneuver is supine and the second maneuver is less than fully upright and the elements of the calibration matrix are calculated using $s_p$, $c_p$, $s_r$, and $c_r$ using equations (27), and using $s_y$, $c_y$ using the equations (36). At block 950, the calibration matrix can be used to determine subsequent subject posture from subsequent sensor output.

Figure 10:
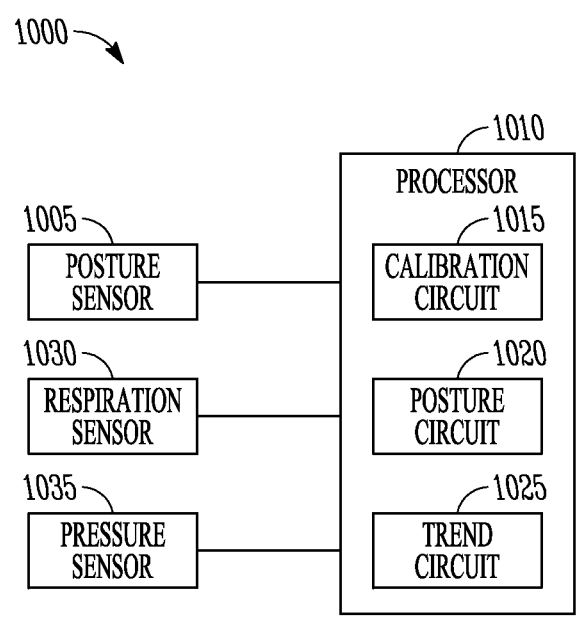
FIG. 10 is a block diagram of an example of portions of a device capable of determining a calibration matrix for a multi-dimensional posture sensor.

FIG. 10 is a block diagram of an example of portions of a device 1000 capable of determining a calibration matrix for a multi-dimensional posture sensor. In some examples, the device can be an implantable medical device, and in some examples the device 1000 can be a wearable medical device. The multi-dimensional posture sensor 1005 provides an electrical sensor output representative of alignment of respective first, second, and third non-parallel axes of the device 1000 with the gravitational field of the earth. In some examples the posture sensor 1005 provides an output for each of the first, second, and third non-parallel axes of the device 1000. The device 1000 includes a processor 1010, such as a microprocessor, digital signal processor (DSP), or other kind of processor. In certain examples, the processor 1010 can be an application specific integrated circuit (ASIC).

The processor 1010 can be communicatively coupled to the posture sensor 1005. The communicative coupling allows the processor 1010 to transmit and/or receive signals to or from the posture sensor 1005 even though there may be intervening circuitry. The processor 1010 includes circuits to perform the functions described herein. The circuits can be hardware, firmware, or software, or any combination of hardware, firmware, and software. In certain examples, the processor 1010 performs instructions embodied in software, firmware, or hardware. In certain examples, the processor 1010 includes a sequencer that proceeds through logic functions implemented by hardware. One or more functions may be performed by one circuit.

The processor 1010 includes a calibration circuit 1015 and a posture circuit 1020. According to some examples, the calibration circuit 1015 and the posture circuit 1020 are configured to perform any of the methods described in regard to FIG. 6. In some examples, the calibration circuit 1015 measures a first sensor output for the first device axis while the subject is in a first specified posture, measures a second sensor output for one of the second device axis or the third device axis while the subject is in the first specified posture, and measures a third sensor output for the first device axis while the subject is in a second specified posture.

In certain examples, the first posture can be an upright posture and the second posture can be the supine posture. The first device axis can be the "u" device axis of FIG. 4 and the second and third device axes can be the "v" and "w" device axes. In certain examples, the first posture is the supine posture and the second posture is an upright posture.

The first device axis can be the "w" device axis of FIG. 4 and the second and third device axes can be the "u" and "v" device axes.

The calibration circuit 1015 calculates the posture sensor 1005 by calculating a calibration transformation using the first and second sensor outputs and transformed sensor outputs. In some examples, the calibration circuit 1015 calculates elements of a matrix used to calibrate the posture sensor 1005 using the first, second, and third sensor outputs. As shown above in regards to equations (26) and (27) the calibration circuit 1015 is able to calculate the elements without determining an orientation angle of the device and without using trigonometric functions. After calibration, the posture circuit 1020 determines a subsequent posture of the subject using the posture sensor 1005.

According to some examples, the calibration circuit 1015 and the posture circuit 1020 are configured to perform any of the methods described in regard to FIG. 9. As before, the calibration circuit 1015 measures a first sensor output for the first device axis while the subject is in a first specified posture, measure a second sensor output for one of the second device axis or the third device axis while the subject is in the first specified posture, and measure a third sensor output for the first device axis while the subject is in a second specified posture.

The two specified postures can be non-orthogonal. In certain examples, the first posture can be an upright posture and the second posture can be a posture more supine than the upright posture but less than fully supine. In certain examples, the first posture can be the supine posture and the second posture can be a posture more upright than the supine posture but less than fully upright.

In addition to the first three measurements the calibration circuit measures a fourth sensor output for the second device axis while the subject is in the second specified posture and measures a fifth sensor output for the third device axis while the subject is in the second specified posture. The calibration circuit 1015 then performs coordinate transformations to generate transformed sensor outputs for the second specified posture.

In some examples, the calibration circuit 1015 calculates a first coordinate transformation associated with a first orientation angle using a first sensor output, and calculates a second coordinate transformation associated with a second orientation angle using the first sensor output and a second sensor output. In certain examples, the transformations are performed using first and second rotation matrices. The transformed sensor outputs are generated by multiplying the third, fourth, and fifth sensor outputs by the first and second rotation matrices. Examples are described above in regard to equations (31) and (35). In certain examples, the calibration circuit 1015 calculates elements of the first rotation matrix using the first sensor output and calculates elements of the second rotation matrix using the first sensor output and the second sensor output.

The calibration circuit 1015 then calculates the elements of the calibration matrix using the first and second sensor outputs and using the transformed sensor outputs. In some examples, the calibration circuit calculates the matrix elements using matrix components (or coefficients) $s_p, c_p, s_r, c_r, s_y$, and $c_y$. The first set of matrix components, $s_p$ and $c_p$, is associated a first orientation angle (e.g., $\theta_p$, or $\theta_{p'}$) and is calculated using the first sensor output, such as by equations (26) or equations (27).

Depending on which set of postures, and therefore which set of equations are used, the second set of matrix components can be either $s_r$ and $c_r$, or $s_y$ and $c_y$, associated with a second orientation angle (e.g., $\theta_r$ or $\theta_{y'}$ respectively). The second set of matrix components is calculated using the first sensor output and the second sensor output, such as by equations (26) or (27). Note that the equations indicate that there is a choice over which sensor measurement to use as the second sensor output. Theoretically, either choice should produce identical results, but in practice one choice can be more desirable due to inaccuracies in the patient maneuver or noise in the measurements during the maneuver.

The third set of matrix components can be either $s_y$ and $c_y$, or $s_r$ and $c_r$, associated with a second orientation angle (e.g., $\theta_y$ or $\theta_{r'}$ respectively). The third set of components is calculated using the transformed sensor outputs, such as by equations (32) or (36). The first, second, and third sets of matrix components $s_p, c_p, s_r, c_r, s_y$, and $c_y$ are then used to calculate the matrix elements of the calibration matrix M, such as the matrix elements in equations (9) and (11), or equations (22) and (24). Note that the matrix components, and therefore the matrix elements, are calculated using the resulting algebraic equations, and are calculated without a determination of any of the orientation angles of the device 1000 or using trigonometric functions. This can reduce the amount of processing power required by the processor 1010.

According to some examples, the posture circuit 1020 receives a sensor output (e.g., a DC-responsive voltage level) for each of the three non-parallel axes of the posture sensor 1005 and compares the sensor outputs to specified sensor output thresholds to determine posture of the subject. The calibration circuit 1015 adjusts the specified sensor output thresholds using the calculated elements of the calibration matrix.

In some examples, the posture circuit 1020 determines subject posture by calculating $$\begin{bmatrix} a_x \\ a_y \\ a_z \end{bmatrix} = M^{-1} \begin{bmatrix} a_u \\ a_v \\ a_w \end{bmatrix}, \quad (37)$$

where $M^{-1}$ is the inverse of the calibration matrix determined by the calibration circuit, $a_u, a_v, a_w$, are the sensor outputs for each of three orthogonal axes of the multi-dimensional sensor, and $a_x, a_y, a_z$, are the corresponding measurements or values in the body coordinate system. The posture circuit 1020 compares the body coordinate measurements to specified thresholds to determine the posture of the subject.

According to some examples, the processor 1010 includes a trend circuit 1025 that trends a posture of the subject. The device 1000 provides an indication of progression of heart disease of the subject at least in part according to the trend. For example, a patient may, due to progression of heart disease, assume a more upright resting position over time. The processor 1010 can initiate sending an indication (e.g., an alert or alarm) to a user or process (e.g., a process executing in an external programmer or at a remote system) of the progression of the disease.

In some examples, the device 1000 includes a respiration sensor 1030 communicatively coupled to the processor 1010. An example of a respiration sensor is a transthoracic impedance sensor used to measure minute respiration volume or tidal volume. An approach to measuring transthoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety. The respiration sensor provides a signal representative of respiration of the subject. The processor 1010 calculates tidal volume of the subject using the respiration signal. The trend circuit 1025 trends the tidal volume of the subject according to a determined posture of the subject.

In some examples, the device 1000 includes an arterial pressure sensor 1035 communicatively coupled to the processor 1010. An example of an arterial pressure sensor includes a pulmonary arterial (PA) pressure sensor. PA pressure includes the pressure within a pulmonary artery due to blood leaving the right ventricle through the pulmonary valve and going to the lungs. In some examples, the arterial pressure sensor provides a signal representative of PA pressure of the subject. The trend circuit 1025 trends PA pressure of the subject according to a determined posture of the subject. In some examples, the processor 1010 detects episodes of low blood pressure or high blood pressure using the pressure signal. The trend circuit 1025 trends episodes of low or high blood pressure according to a determined posture of the subject.

Posture sensing in an implantable or a wearable medical device allows improved monitoring of heart failure patients. Proper calibration of the posture sensor removes variation of the orientation of the sensor due to patient anatomy and due to device migration.

ADDITIONAL NOTES

The above detailed description includes references to the accompanying drawings, which form a part of the detailed description. The drawings show, by way of illustration, specific embodiments in which the invention can be practiced.

These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A medical device deployable by being worn by, or implanted in, a subject, the device comprising:
    a multi-dimensional posture sensor configured to provide an electrical sensor output representative of alignment of respective first, second, and third axes of the device with the gravitational field of the earth while the device is deployed; and
    a processor communicatively coupled to the posture sensor and including:
    a posture calibration circuit configured to:
    measure a first sensor output for the first device axis and a second sensor output for one of the second or third device axes for a first specified posture of the subject;
    calculate first transformation components using the first and second sensor outputs;
    measure additional sensor outputs for the first, second, and third device axes for a second specified posture of the subject;
    calculate second transformation components using the first transformation components and the additional sensor outputs; and
    calculate elements of a calibration matrix using the first and second transformation components; and
    a posture circuit configured to determine a subsequent posture of the subject using outputs of the posture sensor and the calibration matrix.

2. The device of claim 1 wherein the calibration circuit is configured to:
    calculate, using the first sensor output, a first coordinate transformation associated with a first orientation angle;
    calculate, using the first sensor output and the second sensor output, a second coordinate transformation associated with a second orientation angle;

measure third, fourth, and fifth sensor outputs for respective first, second, and third device axes while the subject is in the second specified posture; and transform the third, fourth, and fifth sensor outputs using the first and second coordinate transformations.

3. The device of claim 2, wherein the calibration circuit is configured to:

calculate elements of a first rotation matrix using the first sensor output;

calculate elements of a second rotation matrix using the first sensor output and the second sensor output; and multiply the third, fourth, and fifth sensor outputs by the first and second rotation matrices to transform the sensor outputs.

4. The device of claim 1, wherein the calibration circuit is configured to calculate a calibration transformation by calculating elements of a calibration matrix.

5. The device of claim 4, wherein the calibration circuit is configured to:

calculate, using the first sensor output, a first set of matrix components related to a first orientation angle;

calculate, using the first sensor output and one of the second sensor output or the third sensor output, a second set of matrix components related to a second orientation angle;

calculate, using the transformed sensor outputs, a third set of matrix components related to a third orientation angle; and calculate the elements of the calibration matrix using the first, second, and third sets of matrix components.

6. The device of claim 5, wherein the first orientation angle is associated with a pitch angle, the second orientation angle is associated with a roll angle, and the third orientation angle is associated with a yaw angle.

7. The device of claim 5, wherein the first orientation angle is associated with a pitch angle, the second orientation angle is associated with a yaw angle, and the third orientation angle is associated with a roll angle.

8. The device of claim 1, wherein the posture circuit is configured to:

receive a sensor output for each of the three non-parallel axes of the posture sensor;

transform the sensor outputs using the calibration transformation; and compare the transformed sensor outputs to specified thresholds to determine posture of the subject.

9. The device of claim 1, wherein the first posture is an upright posture, and the second posture is more supine than the first posture and less than fully supine.

10. The device of claim 1, wherein the first posture is a supine posture, and the second posture is more upright than the first posture and less than fully upright.

11. A method of controlling operation of a medical device deployable by being worn by, or implanted in, a subject, the method comprising:

determining a calibration transformation for a multi-dimensional posture sensor by a two posture process including:

measuring a first sensor output for a first device axis and a second sensor output for one of a second device axis or a third device axis for a first specified posture of the subject;

calculating first transformation components using the first and second sensor outputs;

measuring additional sensor outputs for the first, second and third device axes for a second specified posture;

calculating second transformation components using the first transformation components and the additional sensor outputs; and calculating elements of a calibration matrix using the first transformation components and the second transformation components; and determining subsequent subject posture using subsequent calibrated posture sensor output and the calibration matrix.

12. The method of claim 11, wherein calculating the coordinate transformations includes:

calculating, using the first sensor output, a first coordinate transformation associated with a first orientation angle;

calculating, using the first sensor output and the second sensor output, a second coordinate transformation associated with a second orientation angle; and wherein measuring sensor outputs for the first, second and third device axes includes measuring third, fourth, and fifth sensor outputs for respective first, second and third device axes while the subject is in the second specified posture; and wherein transforming outputs includes transforming the third, fourth, and fifth sensor outputs using the first and second coordinate transformations.

13. The method of claim 12, wherein calculating the first coordinate transformation includes calculating elements of a first rotation matrix using the first sensor output, wherein calculating the second coordinate transformation includes calculating elements of a second rotation matrix using the first sensor output and the second sensor output; and wherein transforming the third, fourth, and fifth sensor outputs includes multiplying the third, fourth, and fifth sensor outputs by the first and second rotation matrices to transform the sensor outputs.

14. The method of claim 11, wherein calculating a calibration transformation includes calculating elements of a calibration matrix, and wherein using the calibration to determine subsequent subject posture includes using the calibration matrix to determine subsequent subject posture from subsequent sensor output.

15. The method of claim 14, wherein calculating elements of a matrix to calibrate the posture sensor using the sensor outputs includes:

calculating a first set of matrix components related to a first orientation angle using the first sensor output;

calculating a second set of matrix components related to a second orientation angle using the first sensor output and the second sensor output;

calculating a third set of matrix components related to a third orientation angle using the transformed sensor outputs; and calculating the elements of the calibration matrix using the first, second, and third sets of matrix components.

16. The method of claim 15, wherein calculating a first set of matrix components related to a first orientation angle includes calculating a first set of matrix components associated with a pitch angle, wherein calculating a second set of matrix components related to a second orientation angle includes calculating a second set of matrix components associated with a roll angle, and wherein calculating a third set of matrix components related to a third orientation angle includes calculating a second set of matrix components associated with a yaw angle.

17. The method of claim 15,
wherein calculating a first set of matrix components related to a first orientation angle includes calculating a first set of matrix components associated with a pitch angle,
wherein calculating a second set of matrix components related to a second orientation angle includes calculating a second set of matrix components associated with a yaw angle, and
wherein calculating a third set of matrix components related to a third orientation angle includes calculating a second set of matrix components associated with a roll angle.

18. The method of claim 11, wherein using the calibration to determine subsequent subject posture includes:
receiving a sensor output for each of three orthogonal axes of the multi-dimensional sensor;
transforming the sensor outputs to body coordinate values using the calibration transformation; and
comparing the sensor outputs to specified thresholds to determine the posture.

19. The device of claim 1, wherein the second specified posture is a posture non-orthogonal to the first specified posture.

20. The method of claim 11, wherein the second specified posture is a posture non-orthogonal to the first specified posture of the subject.

* * * * *